(12) United States Patent
Akinwale et al.

(10) Patent No.: US 11,568,973 B1
(45) Date of Patent: *Jan. 31, 2023

(54) AUTOMATED PHARMACY TRANSLATION ENGINE FOR PRESCRIPTION MEDICATION INSTRUCTIONS

(71) Applicant: WALGREEN CO., Deerfield, IL (US)

(72) Inventors: Tolu P. Akinwale, Des Plaines, IL (US); Mohsin O. Ansari, Highland Park, IL (US); Jon Arends, Chicago, IL (US); Donnamarie A. Christie, Orlando, FL (US); David M. Jennings, Winnetka, IL (US)

(73) Assignee: WALGREEN CO., Deerfield, IL (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/169,640

(22) Filed: Feb. 8, 2021

Related U.S. Application Data

(63) Continuation of application No. 14/845,489, filed on Sep. 4, 2015, now Pat. No. 11,011,259.

(51) Int. Cl.
*G16H 20/10* (2018.01)
*G16H 70/40* (2018.01)

(52) U.S. Cl.
CPC ............ *G16H 20/10* (2018.01); *G16H 70/40* (2018.01)

(58) Field of Classification Search
None
See application file for complete search history.

(56) References Cited

U.S. PATENT DOCUMENTS

| | | | |
|---|---|---|---|
| 6,954,729 B2 | 10/2005 | Lee et al. | |
| 2005/0182656 A1 | 8/2005 | Morey | |
| 2009/0099870 A1* | 4/2009 | Wilkinson | G06F 40/274 |
| | | | 705/3 |
| 2012/0016687 A1 | 1/2012 | Dhavle et al. | |
| 2015/0088557 A1 | 3/2015 | Huynh et al. | |
| 2017/0053094 A1 | 2/2017 | Hoenick et al. | |

OTHER PUBLICATIONS

Jeetu G et al., Prescription Drug Labeling Medication Errors: A Big Deal for Pharmacists, Journal of Young Pharmacists, vol. 2, Issue 1, 2010, pp. 107-111, ISSN 0975-1483, https://doi.org/10.4103/0975-1483.62218. (Year: 2010).*

(Continued)

*Primary Examiner* — Devin C Hein
(74) *Attorney, Agent, or Firm* — Marshall, Gerstein & Borun LLP; Randall G. Rueth

(57) ABSTRACT

A system, apparatus, and method for providing an automated translation engine for translating a prescription into a standardized format is generally disclosed. More particularly, embodiments described in this disclosure relate to a system, apparatus, and method for automatically receiving a prescription form, analyzing information provided on the prescription form, and translating the information into a standardized form that details medication information including medication administration directions that are easy for a reader to understand.

20 Claims, 22 Drawing Sheets

(56) References Cited

OTHER PUBLICATIONS

NCPDP, NCPDP Recommendations and Guidance for Standardizing the Dosing Designations on Prescription Container Labels of Oral Liquid Medications, Verision 1.0, Mar. 2014, https://ncpdp.org/NCPDP/media/pdf/WhitePaper/DosingDesignations-OralLiquid-MedicationLabels.pdf (Year: 2014).*
Non-Final Office Action for U.S. Appl. No. 14/845,489 dated Mar. 7, 2019.
Non-Final Office Action for U.S. Appl. No. 14/845,489 dated Sep. 3, 2019.
Final Office Action for U.S. Appl. No. 14/845,489 dated Jan. 10, 2020.
Non-Final Office Action for U.S. Appl. No. 14/845,489 dated May 14, 2020.
Final Office Action for U.S. Appl. No. 14/845,489 dated Sep. 18, 2020.
Notice of Allowance for U.S. Appl. No. 14/845,489 dated Jan. 22, 2021.

* cited by examiner

501

Pre-processing Rules i. Convert Transmitted Input SIG into Uppercase: After Each Step Below, Extra Spaces will be Replaced with Single Space.

ii. Handling Special Characters: Introduce White-space Before & After Certain Special Characters for Better Tokenizing (Like Semicolon, Brackets...etc.). and Also Replacing Certain Chars to Different Form. List of Replacements as Shown Below-

| Original Value | Replacement Value | Input SIG | Modified Input SIG |
|---|---|---|---|
| ";" | " ; " | As Needed(PRN); 2 Puffs Via Spacer Tube Q 6H PRN Wheeze | As Needed (PRN) 2 Puffs Via Spacer Tube Q 6H PRN Wheeze |
| "\\(" | " ( " | 3 Tabs(60MG) PO daily X4Days | 3 Tabs 60MG) PO Daily X4Days |
| "\\(" | " ) " | Take 1 Appful Once A Day (At Bedtime) Intravaginally | Take 1 Appful Once a Day (At Bedtime Intravaginally |
| "\\^" | " ^ " | 500 MG T.I.D for 7 Days^ May Take with Food | 500 MG T.I.D. for 7 Days May Take with Food |
| ":" | " . " | 1 Tab Oral Q6HR,PRN :As Needed For Pain | 1 Tab Oral Q6HR, PRN as Needed for Pain |
| "#" | " # " | Apply to Affected Areas QD-BID as Tolerated. #50 Grams. | Apply to Affected Areas QD-BID as Tolerated. 50 Grams. |
| "\"" | " \" " | Inject "1ML" Intramuscularly | Inject 1 ML Intramuscularly |
| "=" | " = " | 2,000 Units=2 Cap PO QDay | 2,000 Units 2 Cap PO QDay |
| "\\(S\\)" | "" | Take 1 Spray(S) Once A Day | Take 1 Once a Day |
| "Q/" | "Q" | 5 CC POI Q/6HR for 10 Days | 5 CC POI for 10 Days |
| "\\.\\s+" | "." | Two P.O. Q. A.M. | Two P.O. |
| "\\s*/\\s*Day" | " Per Day" | Test 2X/Day & As Needed; | Test 2X & as Needed; |

Pre-processing Rules iii. Remove Commas if it is Used in Numeric Representation, Examples Shown Below -

| Input SIG | Modified Input SIG |
|---|---|
| 2,000 Units=2 CAP PO QDAY | 2000 Units = 2 CAP PO QDAY |
| Take 1 Capsule (50,000 Units Total) by Mouth | Take 1 Capsule (50,000 Units Total) by Mouth | iv. If Hyphen (-) is Used to Represent Range, then Replace it with "TO", Examples Shown Below -

| Input SIG | Modified Input SIG |
|---|---|
| Inhale 2 Puff by Inhalation Route Every 4 - 6 Hours | Inhale 2 Puff by Inhalation Route Every 4 to 6 Hours |
| Inhale 1-2 Puffs Daily | Inhale 1 to 2 Puffs Daily | v. If Slash (/) is Used Between Non-numeric Characters, then Introduce Space Before and After Slash (/). Examples Shown Below -

| Input SIG | Modified Input SIG |
|---|---|
| Take 1 Tablet by Mouth for Anxiety/Sleep | "Take 1 Tablet by Mouth for Anxiety / Sleep" | vi. If a word has Both Numeric and Non-numeric Characters, then Introduce Space Between them. Examples Shown Below -

| Input SIG | Modified Input SIG |
|---|---|
| 1 TAB PO Q24H | 1 TAB PO Q 24 H | vii. If Char "X" Followed by Numeric Value, then Replace "X" with "FOR"

| Input SIG | Modified Input SIG |
|---|---|
| 3 TABS(60MG) PO Daily X4 Days | 3 TABS(60MG) PO Daily For 4 Days | viii. If Char "X" Prefixed with Numeric Value, then Replace "X" with "TIMES"

| Input SIG | Modified Input SIG |
|---|---|
| Take 5 ML by Oral Route 3X Daily | Take 5 ML by Oral Route 3 Times Daily |

FIG. 6

Pre-processing Rules xi. Replace Other Abbreviations: Replace Other Abbreviation Like Synonyms etc. in the Input Sig by Matching the Data with the Corresponding Matching Words/Phrases which are Maintained in the Data Dictionary "Synonyms / Other Abbreviations" in the eRx Database. We can Enhance this File to Replace Same Meaning Words/phrase to a Unique Form for Better Parsing.

| Input SIG | Modified Input SIG |
|---|---|
| Take 1 Tablet PO Twice Daily W/Food | Take 1 Tablet By Mouth Twice Daily With Food |
| 1 Q 8 HRS X 10 Days | 1 Every 8 by Mouth for 10 Days | x. Replace Latin Abbreviations: Replace the Latin Occurrences in the Input Sig by Matching the Data with the Corresponding English Phrases which are Maintained in the Dictionary "Latin Abbreviations" in the eRx Database.

| Input SIG | Modified Input SIG |
|---|---|
| Take 1 Tablet PO Twice Daily | Take 1 Tablet by Mouth Twice Daily |
| 110 MCG INH QPM | 110 MCG Inhale Every Evening | xi. Replace Number Words to Digits

| Input SIG | Modified Input SIG |
|---|---|
| One Tablet TID | 1 Tablet 3 Times Daily |
| Take Two Capsules by Mouth Three Times Daily | Take 2 Capsules by Mouth 3 Times Daily | xii. Introduce White-space Before & After Dot (.) & Comma (,) Characters for Better Tokenizing Don't Change Dot(.) if it is in Numeric Representation.

| Input SIG | Modified Input SIG |
|---|---|
| Take 1 Capsule(s) Every Day by Oral Route for 30 Days | Take 1 Capsule Every Day by Mouth Route for 30 Days . |
| 1 Cap(S) PO Daily, X90 Day(s) | 1 Capsule by Mouth Daily , for 90 Day | xiii. Check the Values within the Brackets(), and if Same Value Present Before Bracket Starts then Considering it as Duplicate Value and Removing one of it. (E.g."2 (2)" will be Converted to "2").

| Input SIG | Standardized Input SIG | Modified Input SIG |
|---|---|---|
| 1(One) Capsule , Oral , QID X 10 Days | 1(1) , Capsule Mouth , 4 Times Daily for 10 Days | 1 Capsule , Mouth , 4 Times Daily for 10 Days |
| Take 1 Tablet QDay (Every Day) | Take 1 Tablet Every Day (Every Day) | Take 1 Tablet Every Day |

Core Parsing Rules i. Parse Miscellaneous Notes - Miscellaneous Notes will follow Certain Prefixes and will be Configured in Data Dictionary "Instruction Prefix". This Step will Identify Phrases which Start with those Prefixes Using Regex Rules, if Found then the Process will Take the Rest of the Text and Tag it into Miscellaneous Notes Attribute and Remove it from the Input SIG.

| Input String | Miscellaneous Notes |
|---|---|
| 6 ML Oral Daily, X4 Day(s), Instr:Start On 08/21/2014 | Instr:Start on 08/21/2014 |
| Apply Topically 2 Times Daily. Max is 2 Weeks. | Max is 2 Weeks | ii. Parse Admin Timings - This Step Will Identify Admin time Patterns (Like 7 PM, 8 AM...etc.) Using Configured Data Dictionary "Admin Time Suffix" and Regex Rules, it Found Tag it into Admin Timings Attribute and Remove if from the Input SIG.

| Input String | Standardized String After Pre-Processing | Frequency | Admin Timings |
|---|---|---|---|
| Take 1 Tablet Daily in the | Take 1 Tablet Daily in the Morning | Daily | Morning |
| Take 1 Capsule(20MG) By Oral Route Every Day at 3 Pm | Take 1 Capsule (20 MG) by Mouth Route Every Day at 3 Evening | Every Day | 3:00 Pm | iii. Parse Frequency - Frequency Values will Follow Certain Patterns (Numeric_Pattern + Suffix, Every + Numeric_Pattern + Suffix, Every + Numeric_Pattern), and Suffixes will be Configured in Data Dictionary "Frequency Suffix" and "Frequency Suffix with Every". This step will Identify Phrases which follow these Patterns Using Regex Rules, if Found then Tag it into Frequency Attribute and Remove it from the Input SIG.

| Input String | Standardized String | Frequency | Frequency Value | Frequency Unit |
|---|---|---|---|---|
| Inhale 1 Puff(S) Twice a day by Inhalation Route for 30 Days. | Inhale 1 Puff 2 times a day by Mouth Route for 30 Days. | 2 Times a Day | 2 | Day |
| Take 1 Capsule PO 3 X A Day | Take 1 Capsule by Mouth 3 Times A Day | 3 Times a Day | 3 | Day |

Core Parsing Rules iv. Parse Drug Strength - This Step will Identify Drug Strength Using Configured Data Dictionary "Strength Units" and Regex Rule (Numeric_Pattern + Strength_Units), if Found Tag it into Drug Strength Attribute and Remove it from the Input SIG.

| Input String | Strength Value | Strength Unit |
|---|---|---|
| Take 1.5 GM by Mouth Every 6 Hours as Needed | 1.5 | GM |
| 60 MG PO BID | 60 | MG | v. Parse Dosage Info - This Step will Identify Dosage Quantity and Dosage Form Using Configured Data Dictionary "Dosage Forms" and Regex Rule (Numeric_Pattern + Dosage_Form), if Found Tag it Into Dosage Attribute and Remove it from the Input SIG.

| Input String | Dosage Value | Dosage Unit |
|---|---|---|
| Take 1 Tablet by Mouth Daily | 1 | Tablet |
| Apply 1 Patch to Skin Every 72 Hours for Pain | 1 | Patch | vi. Parse Duration - This Step will Identify Duration Using Configured Data Dictionary "Duration Metrics" and Regex Rule (Numeric_Pattern + Duration_Form), if Found Tag it into Duration Attribute and Remove it from the Input SIG.

| Input String | Duration Value | Duration Unit |
|---|---|---|
| Take 1.5 ml by Mouth Every 6 Hours as Needed | 10 | Days |
| Topical Apply Daily to Affected Area X2 Weeks | 2 | Weeks |

Core Parsing Rules vii. Match with Dictionary Data - This Step will Match Remaining Phrases Against Configured Data Dictionary "Token Category" and Tag Identified Phrases into Respective Attribute category.

It will Use Ngram Technique to Generate Possible Phrases for Comparison. The Input SIG is Being Converted into a Series of Combination of Words Known as N-Grams where "N" is the Number of Words we are Taking Together for Making a Combination. The Combinations will be Linear one, Starting from the Beginning Word of the Sentence Till the End. E.g Take 1 Tablet by Mouth Daily will be Converted into N-Gram (N=5) Tokens as Follows:

| Number of N-Gram | Tokens |
|---|---|
| 5 | Take 1 Tablet by Mouth, 1 Tablet by Mouth Daily |
| 4 | Take 1 Tablet by,1 Tablet by Mouth, Tablet by Mouth Daily |
| 3 | Take 1 Tablet,1 Tablet by, Tablet by Mouth, by Mouth Daily |
| 2 | Take 1, 1 Tablet, Tablet by, by Mouth, Mouth Daily |
| 1 | Take 1, Tablet, by, Mouth,Daily |

The Generated Token are Now Considered One by One for Matching with Data Dictionary Starting with the Largest N-Gram. Once the Tokens are Matched, the whole Phrase will be Tagged into Matched Attribute and Removed from the Input SIG.and N-Gram Tokens will be Generated Again for Remaining SIG and the Matching will Proceed with Rest of the Tokens for the Rest of the N-Grams.

| Input String | Verb | Dosage Value | Dosage Unit | Route of Admin | Frequency | Frequency Unit |
|---|---|---|---|---|---|---|
| Take1 Tablet By Mouth Daily | Take | 1 | Tablet | Mouth | 1 | Day |

Core Parsing Rules viii. Other Parsing – Many of input SIG Follow Patterns Like "1 by Mouth Daily", without Dosage from with Dosage Unit. This Step will Check Weather Remaining SIG Begins with Numeric Pattern, if it is, then Considering it as Dosage Value and Tag it into Dosage Attribute. The above Logic is Implemented as a Part of POC. In the Final Solution there is a Need to Validate Whether the Logic Map Values to Wrong Attributes by Referring More Examples.

| Input String | Input Dosage form Code | Verb | Dosage Value | Dosage Unit | Route of Admin | Frequency | Frequency Unit |
|---|---|---|---|---|---|---|---|
| 1 By Mouth Daily | Tabs | Take | 1 | Tablet | Mouth | 1 | Day |

Post-processing Rules

I. Identify Non-parsed Tokens - This Step will Remove Ignorable Tokens (like a, an, the...etc.) from Remaining Non-parsed String, if Any Remaining Non-parsed Portion Exist then Tag it as a "Unknown Word/Value". Ignorable Tokens are Configured in Data Dictionary "Ignorable Tokens".

| Input String | Unknown Words/Values | Ignorable tokens |
|---|---|---|
| Apply to Vaginal Area 1 Time Per Day | Apply Area | To | ii. Calculate Frequency Values - this Step will Parse Frequency Attribute into Low/High Frequency Values and Frequency Unit and Tag them into Respective Attribute Category.

| Input String | Low Frequency Value | High Frequency Value | Frequency Unit |
|---|---|---|---|
| Take 2 Puffs by Mouth Twice Daily as Needed | | 2 | Day | iii. Calculate Dosage Values - this Step will Parse Dosage Attribute into Low/High Dosage Values and Dosage Unit and Tag them into Respective Attribute Category.

| Input String | Low Dosage Value | High Dosage Value | Dosage Unit |
|---|---|---|---|
| Place 1-2 Drop in Both Eyes Twice a Day as Needed for Allergies | 1 | 2 | Drop | iv. Calculate Duration Values - this Step will Parse Duration Attribute into Low/High Duration Values and Duration Unit and Tag them into Respective Attribute Category

| Input String | Low Duration Value | High Duration Value | Duration Unit |
|---|---|---|---|
| Apply (1g) by Topical Route 2 Times Every Day for 10 to 14 Days as Discussed Sparingly | 10 | 14 | Days | v. Calculate drug Strength Values - this Step will Parse Drug Strength Attribute into Low/High Strength Values and Strength Unit and Tag them into Respective Attribute Category.

| Input String | Low Strength Value | High Strength Value | Strength Unit |
|---|---|---|---|
| 2 ~ 4 MG QD X 4 | 2 | 4 | MG |

Post-processing Rules vi. Parse Admin Timing From Frequency - this Step will Check "Admin Time Metrics" Values in Parsed Frequency Attribute, if Exist then will Mark it as Admin Time. E.g. Frequency Attribute has"Every Evening" which has Admin Metric Values "Evening" in it. So Evening will be Considered as Admin Time Also.

| Input String | Frequency | Admin Timing |
|---|---|---|
| Take 1 Tablet by Mouth Monthly | Nightly | Night |
| Take 1 Tab by Mouth Every Evening | Every Evening | Evening |

Duplicate Rules

- If Mandatory Tokens and AdminTiming Match then SIG is Considered Duplicate. Identify Duplicates Amongst all the Input SubSIGS and form a Duplicate SIG Grouping.

E.g. Take 1 Tablet Daily in Morning, Take 1 Tablet Every 24 Hours in Morning. In This Case, Both Mandatory Elements (Dose and Frequency) and AdminTiming Match. Hence this is Considered as Duplicate SIG.

1. If within a Duplicate SubSIG Group, Optional Attributes have Conflicting Values then Go for Manual Process.

E.g. Take 1 Twice Daily for 5 Days, Take 1 Twice Daily for 7 Days

In this Case the Two Mandatory Elements (Dose and Frequency) Match but the Duration Conflicts. Hence this SIG will be Marked for Manual Processing 2. If within a Duplicate SubSIG Group, Optional Attributes are Missing in One of SIG and Any Optional Attribute having Same Value, then Merge Optional Attributes Following SIG Order Defined in Data Dictionary.

E.g. 1 Tablet Daily by Mouth, Take 1 Tablet Every 24 Hours.

In this Case the Two Mandatory Elements (Dose and Frequency) Match Verb is Missing in the First SIG and "By Mouth" is Missing in Second SIG Hence these SIG will be Combined to Form Final SIG. Take 1 Tablet Daily by Mouth 3. If within a Duplicate SubSIG Group, if all Optional Attributes Match then Use One.

E.g. Take One by Mouth Daily, Take One Every Day, Take One Tablet Orally Daily. Hence One of SIG will be Used and Remaining Discarded Because All the SubSIGS are Duplicate.

Duplicate Rules

- After Duplicate/Merge Step Above Check for the Missing Duration and Conjunction as Below:

- If the Incoming SIG has Multiple SubSIGS Without any the word "then" will be Added as a Conjunction, but on the Stipulation that a SubSIG Preceding a Conjunction Must have Duration Otherwise the SIG will be Marked for Manual Processing.

E.g. a) Take 1 Daily. Take 2 Daily

In this Case the First SubSIG Does Not have the Duration Hence this will be Marked for Manual.

E.g. b) Take 1 Daily for 7 Days. Take 2 Daily

In this Case the First SubSIG does have a Duration, Hence the Conjunction "then" will be Added and the Resultant SIG will be Take 1 Tablet by Mouth Daily for 7 Days then Take 2 Tablets Daily.

| Detailed Descriptions of the Error Code | Description Shown on Metrics Report | Type of Exception |
|---|---|---|
| The Transmitted SIG is not Fully Parsed, i.e. There are Unknown Word(s)/Phrase(s). | Incomplete Transmitted SIG Parsing | Business |
| If the Number of SubSIGs is Greater than Three (Duplicate or not) | Transmitted SubSIGs Greater than 3 | Business |
| Confidence Score is Below the Threshold | Confidence Score Below Threshold | Business |
| The Mandatory Tokens are Missing in the Transmitted SIG and not All of the Default SIG Usage Conditions Below are Satisfied:<br>- The Product is not a Controlled Drug and<br>- The Product has an Default SIG<br>- The Product is Located in the Configurable Inclusion List and<br>- The Incoming SIG has Nonspecific SIG | Transmitted Parsed Elements Missing and no Default SIG | Business |
| The transmitted Parsed Elements are not Primary or Secondary or Acceptable for the Inferred Elements. | Non-primary/Secondary/Acceptable Transmitted Parsed Elements | Business |

| Detailed Descriptions of the Error Code | Description Shown on Metrics Report | Type of Exception |
|---|---|---|
| The Strength Cannot be Converted to Dose. All Conditions Below are Satisfied:<br><br>- The Product has 1 Active Ingredient<br><br>- The eRx Transmitted SIG Includes a Strength with or without a Dose<br><br>- The Product is not on the Configurable Strength/Dose Conversion Includsion List<br><br>- The Product is not on the Configurable Strength/Dose Conversion Excludsion List<br><br>- The Drug Strength or Unit of Measure (UOM) are Unavailable in the IC+ Drug Table | Missing Strength Value or UOM from Drug Table | Business |
| All Conditions Below are Satisfied:<br>- If The Incoming eRx Transmitted Message Provides a Strength<br>- The Product is on The Inclusion List.<br>- If The Drug Strength Data Is not Available in The IC+ Drug Table<br>- The Product is on the Medispan Drug Table<br>- There are Multiple Active Products within the Same 14-Digit GPI. | Non-Unquie Active Products Using Medispan Strength-Dose Conversion | Business |
| The Selected Product's Route of Administration does not Match the Route of Admin in the Final SIG | Non-Matched Post-parsing Directions-Route of Administration Combination | Business |

| | | |
|---|---|---|
| If a Conjunction is Missing for SubSIGs and the Previous SubSIG does not Contain a Duration | Transmitted First SubSIG Duration or Conjunction Element Missing | Business |
| For SubSIGs, if any Information that is not Mandatory or Admin Timing is Conflicting with the Duplicate SIGs | Conflicting Duplicate SubSIGs | Business |
| The Selected Product's Dosage from cd/type and Route of Administration Combinations are not Provided in the Configurable Mandatory/Inferred table. | Missing Primary/Secondary Parsed Elements for Route of Admin/Dosage Combination | Business |
| The System Must Revert to Manual Process, if the Incoming eRx Message Provides Multiple Frequencies for an Associated SubSIG, for Example: Take One Tablet Twice Daily Twice a Week | Multiple Frequencies for an Associated SubSIG | Business |
| The System must Revert to Manual Process, if the Incoming eRx Message Provides Multiple Time Periods for an Associated SubSIG, for Example: Take One Tablet Every Day Every Week | Multiple Time Periods for an Associated SubSIG | Business |
| The System must Revert to Manual Process if for any Given SubSIG, There are Multiple Values in these Attributes: Verb, Dosage Unit, Strength Value and Unit, Route of Admin, Site of Admin Duration Value and Unit, Conjunction(?) | Multiple Values within a SubSIG | Business |

FIG. 17B

AUTOMATED PHARMACY TRANSLATION ENGINE FOR PRESCRIPTION MEDICATION INSTRUCTIONS

CROSS REFERENCE TO RELATED APPLICATIONS

The present application is a continuation of U.S. patent application Ser. No. 14/845,489, entitled AUTOMATED PHARMACY TRANSLATION ENGINE FOR PRESCRIPTION MEDICATION INSTRUCTIONS, filed Sep. 4, 2016, the disclosure of which is incorporated herein in its entirety by reference.

TECHNICAL FIELD

A system, apparatus, and method for providing an automated translation engine for translating information found on a prescription (e.g., drug administration instructions, patient instructions; medication information, etc.) is generally disclosed. More particularly, embodiments described herein relate to a system, apparatus, and method for automatically receiving an electronic prescription form, analyzing information provided on the electronic prescription form, determining whether the electronic prescription form is reliable enough to proceed through the automated process based on information identified from the electronic prescription form, and translating the information included in the electronic prescription form into a standardized form. When certain prescription information is not found, or does not satisfy one or more predetermined rules, during this analysis, the automated translation engine may revert the translation process back to a manual process to be completed by a person related to a prescription filling process.

It follows that the automated translation engine disclosed herein enables electronic prescription information to be received from remote locations, translated into a standard format, and transmitted to remote locations to be processed and printed as a label for prescription medication packaging. The transmission and translation of electronic prescription information according to the automated translation engine described herein provides a technical solution to the technical issue of providing an accurate and efficient process for producing prescription labels based on electronic prescription information.

BACKGROUND

Patients may be prescribed medication by a medical doctor to address certain ailments the patient may be suffering. In order to then obtain the medication prescribed by the medical doctor, the patient must generally have the prescription filled through a pharmacy, either at a medical facility or retail location. Therefore, the process generally followed by a patient to fill a prescription includes the patient receiving a prescription from a medical doctor, the patient presenting the prescription to a pharmacy, and the pharmacy filling the prescription by identifying the medication described in the prescription and dispensing the medication to the patient. In addition, the pharmacy may provide directions to the patient for taking the medication contents described in the prescription.

This prescription filling process is labor intensive as it requires the pharmacy to read information from the prescription and manually input medication information and medication directions that will be printed on a label for the patient to read on the dispensed medication. Each pharmacy or pharmacist may input the prescription information differently, and so the labels being provided to patients lacked uniformity.

SUMMARY

The present disclosure describes a system, apparatus, and method configured to provide an automated translation engine for receiving a prescription, analyzing information included in the prescription, applying one or more translation rules to the analyzed information, and producing a label in a standardized format that includes medication information and/or medication usage directions.

According to some embodiments, a computing device comprising a data storage unit configured to store a plurality of translation rules and token category definitions, a network interface configured to receive prescription information from a remote computing device, and a processor configured to communicate with the network interface are disclosed. The processor may be configured to control an automated prescription translation engine module to control an automated prescription translation process to: parse the prescription information; in response to the parsing, tag a word included in the prescription information that satisfies a token category definition with a corresponding token; modify the prescription information by modifying the word tagged with the token according to a translation rule corresponding to the token; generate a final instruction wrapper including the modified prescription information; and control the network interface to transmit the final instruction wrapper.

According to some embodiments, a method for automatically translating prescription information is disclosed. The method may comprise: storing a plurality of translation rules and token category definitions in a data storage unit; controlling a network interface to receive prescription information from a remote computing device; enabling communication between a processor and the network interface; and controlling the processor to control an automated prescription translation engine module to control an automated prescription translation process. The processor may control the automated prescription translation process to: parse the prescription information; in response to the parsing, tag a word included in the prescription information that satisfies a token category definition with a corresponding token; modify the prescription information by modifying the word tagged with the token according to a translation rule corresponding to the token; generate a final instruction wrapper including the modified prescription information; and control the network interface to transmit the final instruction wrapper.

These and various other embodiments and aspects will become apparent and be more fully understood from the following detailed description and accompanying drawings, which set forth the illustrative embodiments that are indicative of the various ways in which the principles of the invention may be employed.

This application is defined by the appended claims. The description summarizes aspects of the embodiments and should not be used to limit the claims. Other implementations are contemplated in accordance with the techniques described herein, as will be apparent upon examination of the following drawings and detailed description, and such implementations are intended to be within the scope of this disclosure.

BRIEF DESCRIPTION OF THE DRAWINGS

For a better understanding, reference may be made to embodiments shown in the following drawings. The components in the drawings are not necessarily to scale and related elements may be omitted so as to emphasize and clearly illustrate the novel features described herein. In addition, system components can be variously arranged, as known in the art. In the figures, like referenced numerals may refer to like parts throughout the different figures unless otherwise specified.

FIG. 5 illustrates a table including exemplary pre-processing rules, according to some embodiments;

FIG. 6 illustrates a table including exemplary pre-processing rules, according to some embodiments;

FIG. 7 illustrates a table including exemplary pre-processing rules, according to some embodiments;

FIG. 8 illustrates a table including exemplary core parsing rules, according to some embodiments;

FIG. 9 illustrates a table including exemplary core parsing rules, according to some embodiments;

FIG. 10 illustrates a table including exemplary core parsing rules, according to some embodiments;

FIG. 11 illustrates a table including exemplary core parsing rules, according to some embodiments;

FIG. 12 illustrates a table including exemplary post-processing rules, according to some embodiments;

FIG. 13 illustrates a table including exemplary post-processing rules, according to some embodiments;

FIG. 14 illustrates a table including exemplary duplicate rules, according to some embodiments;

FIG. 15 illustrates a table including exemplary duplicate rules, according to some embodiments;

FIGS. 16A and 16B illustrate a table including exemplary error codes, according to some embodiments;

FIGS. 17A and 17B illustrate a table including exemplary error codes, according to some embodiments;

DETAILED DESCRIPTION OF EXAMPLE EMBODIMENTS

Figure 1:
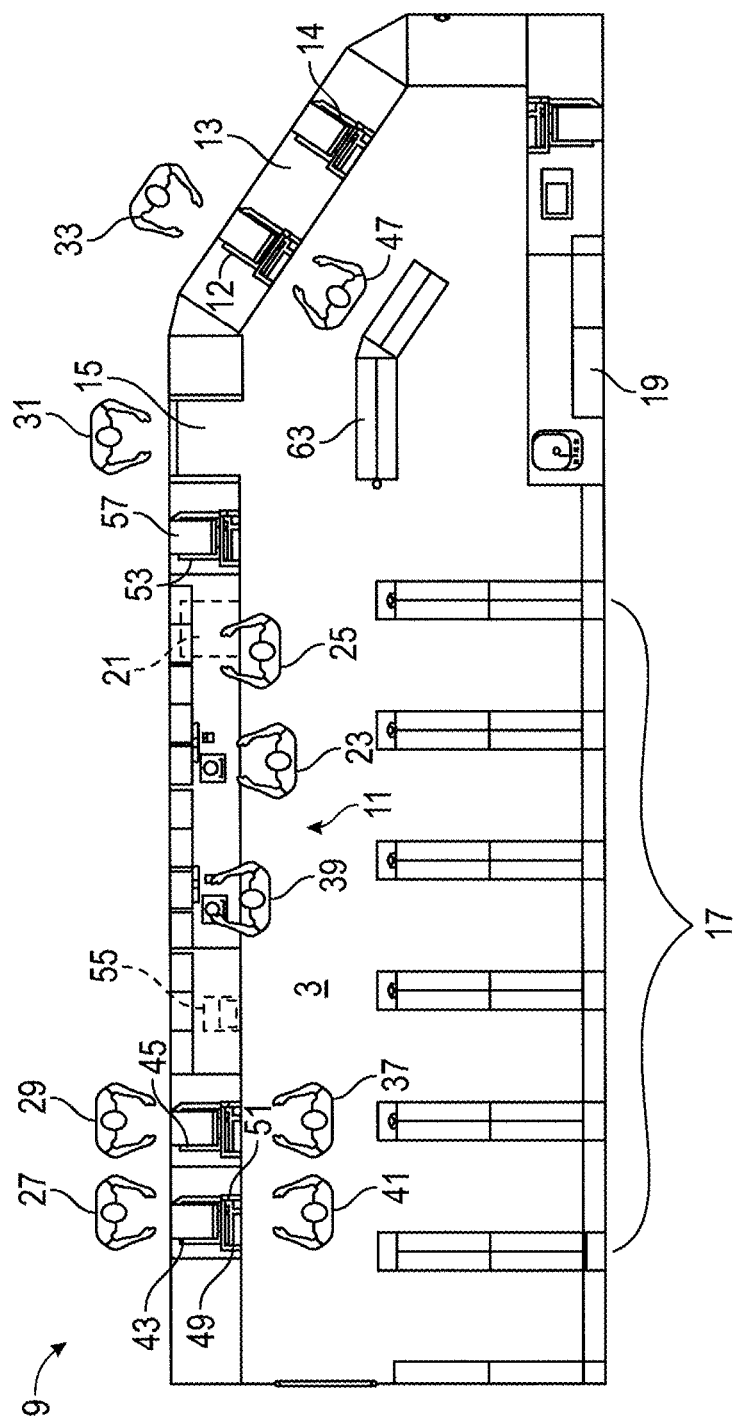
FIG. 1 illustrates an exemplary schematic diagram for a pharmacy operation environment, according to some embodiments.

While the features described herein may be embodied in various forms, there are shown in the drawings, and will hereinafter be described, some exemplary and non-limiting embodiments, with the understanding that the present disclosure is to be considered an exemplification and is not intended to limit specific embodiments. Not all of the depicted components described in this disclosure may be required, however, and some implementations may include additional, different, or fewer components from those expressly described in this disclosure. Variations in the arrangement and type of the components may be made without departing from the spirit or scope of the claims as set forth herein.

The "dispensing" of medication for a prescription involves a process of prescribing, entering, filling, verifying and selling the medication described in the prescription. Because much of the process involves human input and control, a uniform (i.e., standard) result is unlikely to be found. For example, typically when a pharmacy receives a prescription for dispensing a medication, information on the prescription will be manually input to a pharmacy computer in order to produce a medication label for placement on the medication for a reader (e.g., pharmacist, pharmacy technician, doctor, or patient/customer) to read. The medication label may include various medication information such as medication name, medication dosage, physician's identification information, pharmacy identification information, medication dispensing date, patient identification information, controlled substance status, pharmacist identification information and/or medication usage directions including cautionary statements. However, due to the human aspect of this process, the information found on the produced label may not be uniform. This may lead to patient confusion, and the manual labor required to produce the label is time intensive and inefficient.

It follows that an automated prescription translation engine is disclosed for alleviating, at least in part, some of the manual labor of inputting prescription information into the pharmacy computer to produce the medication label. An added benefit is that the automated prescription translation engine is configured to receive a prescription and produce a medication label in a standard format. The standard format of the medication label produced by the automated prescription translation engine will be easily readable and understood by a reader such as a pharmacist, pharmacy technician, doctor, or patient/customer.

A pharmacy management system according to this disclosure will be described with respect to an exemplary and conventional pharmacy layout illustrated in FIG. 1. Specifically, FIG. 1 depicts a pharmacy 3 including an order entry workstation 9, a filling/checking workstation 11, a payment workstation 13 and a consultation workstation 15. Pharmacy 3 is provided with any number of non-automated storage locations at which medications and products are stored for access by pharmacy personnel. For example, pharmacy 3 shown in FIG. 1 is provided with an array of shelf units 17 (e.g., six static storage shelf units). Each shelf unit in the array of shelf units 17 is typically about 6 to 8 feet in height and includes a plurality of spaced-apart horizontally-oriented shelves. Medications and products are stored on each shelf within the array of shelf units 17 pending manual retrieval for fulfillment of a prescription order.

Pharmacy 3 may include other storage locations such as a restricted-access cabinet 19 for storage of narcotics and other controlled medications. Pharmacy 3 may also include a refrigerator 21 for storage of perishable medications and articles.

Pharmacy 3 is staffed by personnel having varying levels of responsibility. The pharmacy staff includes at least one registered pharmacist such as pharmacists 23, 25 illustrated in pharmacy 3. Pharmacists 23, 25 are responsible for fulfillment of prescription orders and for verification of each prescription order before the order is provided to a customer such as customers 27, 29, 31, and 33 illustrated in the pharmacy 3. One or more technicians 37, 39, 41 may be employed to assist pharmacists 23, 25 in fulfilling each prescription order. The pharmacists 23, 25 or technicians 37, 39, 41 may also provide health-care-related information to customers 27, 29, 31, and 33 at consultation workstation 15. A sales clerk 47 may process sales transactions at the payment workstation 13 using computer terminal 14 or 12.

A customer's prescription information may be input into a pharmacy information system either by manual input by a pharmacy employee (e.g., technicians 37, 39, 41), or by electronic communication where an electronic prescription (e.g., eRx) is received and stored into the pharmacy information system. Following adjudication by the pharmacy information system, each adjudicated prescription is stored as an order in a database on pharmacy computer 53 at filling/checking workstation 11 for fulfillment, typically on a first in first out ("FIFO") basis. Labels for attachment to each container associated with the prescription order may be printed on printer 55.

Pharmacist 23, 25 or technician 37, 39, 41 selects the prescription order next in line to be filled from the pharmacy computer 53 of the filling/checking workstation 11. The prescription order, and prescriptions comprising the order, may be displayed on a communications device, such as a display 57 associated with computer 53. The prescriptions making up the prescription orders may be arranged in an order automated by the computer 53, or may not be arranged in any particular sequence.

Workflow at conventional pharmacy 3 may be generally summarized in the following manner. Pharmacist 23, 25 or technician 37, 39, 41, or other pharmacy staff, may receive a prescription order from a customer 27, 29, 31, or 33 and then input the prescription order information to the system at data entry workstation 9 using keyboard 49, computer mouse 51, or other available input command component of computer 43. Following adjudication by the pharmacy information system, each adjudicated order is held in a database on pharmacy computer 53 at filling/checking workstation 11 for fulfillment, typically on a first in first out ("FIFO") basis. Medication labels for attachment to each container associated with the prescription order may be printed on printer 55. An automated prescription translation process for preparing the medication labels is described in further detail with respect to flow chart 300 below.

The pharmacist 23, 25 or technician 37, 39, 41 then fills each prescription in the prescription order. Each prescription in the prescription order is filled by walking to one of the array of shelf units 17 or refrigerator 21 and retrieving the appropriate medication which may be in bulk-form or in prepackaged form. The medication is then taken from one or more of the array of shelf units 17 or refrigerator 21 to the filling/checking work station 11 where the appropriate number of medications are metered into a container, such as a vial, bottle with reclosable cap, box or other type of container capable of holding the medication as intended.

This process is repeated until each prescription in the prescription order is fulfilled. The prescription order is then verified by pharmacist 23, 25 at filling/checking work station 11 to ensure that the correct medication is in each container (e.g., vial, bottle, box, etc.). The fulfilled order may then be placed in a bag or other package and is held at a "will call" area 63 near payment work station 13. Sales clerk 47 processes the transaction and delivers the packaged prescription order to customer 33 at the payment work station 13.

The description of the pharmacy 3 is provided for exemplary purposes only in accordance to some embodiments. It follows that it is within the scope of the innovation described herein to include other embodiments where the pharmacy 3 may include a fewer, or greater, number of components, stations, or employees. For instance, the pharmacy may additionally include a drive-up window such that any one or more of the order entry workstation 9, filling/checking workstation 11, payment workstation 13 and/or consultation workstation 15 may be available at the drive-up window. By including the additional drive-up window, a customer may fill their prescription at the pharmacy 3 without having to leave their vehicle.

Figure 2:
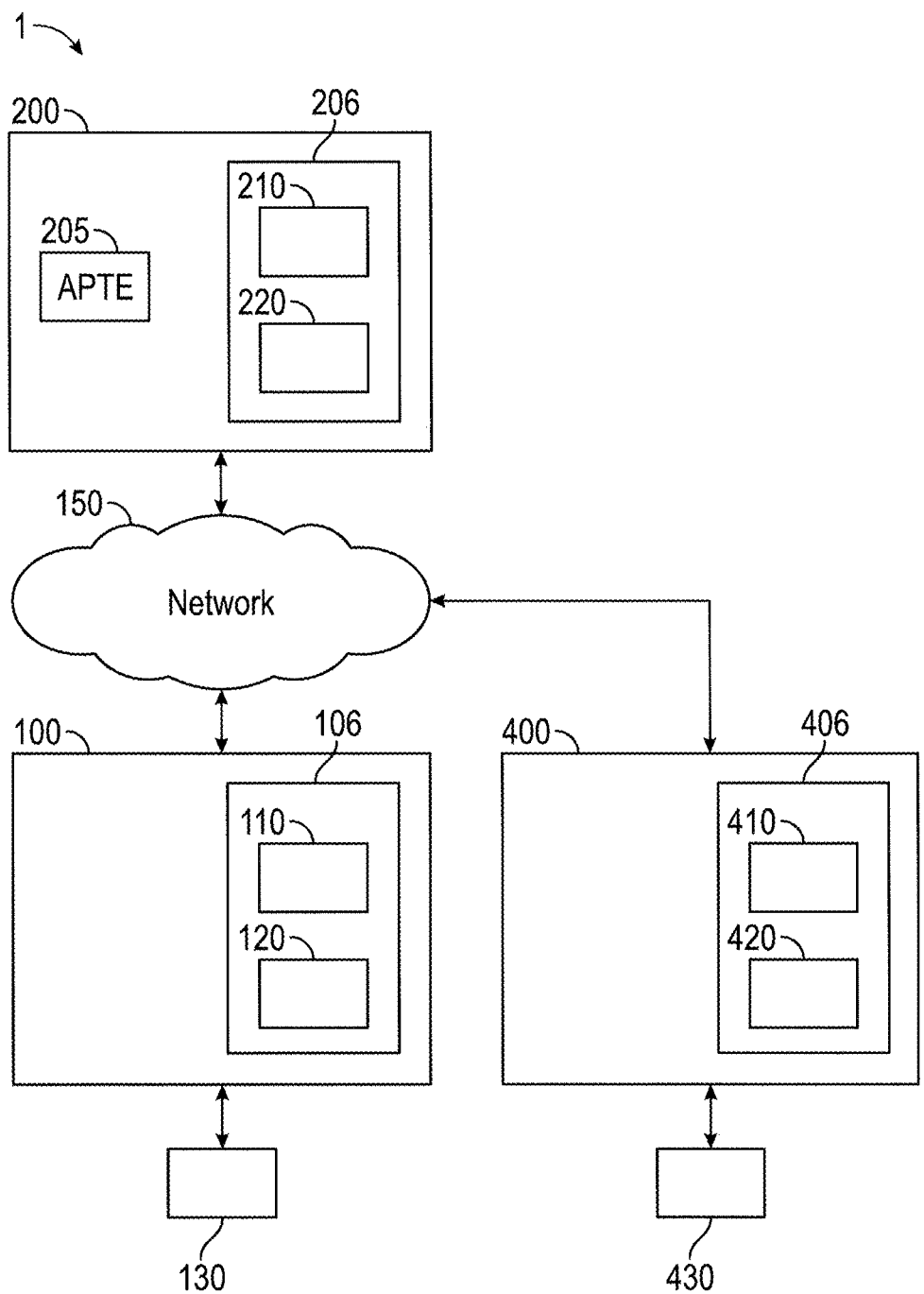
FIG. 2 illustrates an exemplary schematic diagram for a pharmacy management system, according to some embodiments.

FIG. 2 illustrates an exemplary pharmacy management system 1 including pharmacy computer 100, pharmacy management server 200, and medical facility computer 400. Pharmacy computer 100 may be representative of any one or more of the computer terminals 12, 14, 43, 45 or 53 in pharmacy 3. Pharmacy computer 100 may be configured to communicate bi-directionally with pharmacy management server 200 through network 150. Although not specifically illustrated, pharmacy computer 100 and pharmacy management server 200 may include network interfaces configured to enable pharmacy computer 100 and pharmacy management server 200 to communicate (e.g., transmit and receive information) with each other via network 150. Network 150 may represent one or more networks that may be comprised of any combination of one or more of a cellular network, including standards-based networks (e.g., 2G, 3G, Universal Mobile Telecommunications System (UMTS), GSM® Association, Long Term Evolution (LTE)™, or more), WiMAX, Bluetooth, near field communication (NFC), WiFi (including 802.11a/b/g/n/ac or others), WiGig, Global Positioning System (GPS) networks, and other types of communications networks available at the time of the filing of this application or that may be developed in the future. Further, network 150 may be a public network, such as the Internet, a private network, such as an intranet, or combinations thereof, and may utilize a variety of networking protocols now available or later developed including, but not limited to TCP/IP based networking protocols.

Pharmacy computer 100 may be configured to communicate with pharmacy management server 200 in order to transmit prescription information to automated prescription translation engine (APTE) 205 included within pharmacy management server 200. Pharmacy computer 100 may also be configured to communicate with pharmacy management server 200 in order to receive medication label information from APTE 205, where the medication label received from APTE 205 is in a standard format after applying the automated prescription translation process to the prescription information. A more detailed description of the automated prescription translation process implemented by APTE 205 will be provided throughout this disclosure.

The pharmacy computer 100 includes a processing unit 106 comprised of a processor 110 and a memory 120. Memory 120 may store software comprised of executable instructions, where processor 110 is configured to execute the executable instructions to implement any one or more process or method described herein. Pharmacy computer 100 is further in communication with an input device 130, such as a keyboard, mouse, barcode scanner, RFID reader, NFC reader, image scanner, memory slot, or other information input device capable of inputting information (e.g., prescription information) into pharmacy computer 100. A data entry clerk or technician 41 at pharmacy 3 may, for example, input prescription information from the prescription order via the keyboard and mouse, or have an optical character recognition (OCR) process executed on an electronic copy of the prescription order to extract the prescription information. It follows that prescription information may be transmitted directly from pharmacy computer 100 to pharmacy management server 200. The prescription information transmitted to pharmacy management server 200 may be in a known electronic format such as eRx. Once received at pharmacy management server 200, the APTE 205 may process the prescription information according to the automated prescription translation process detail herein. A more detailed description of the automated prescription translation process implemented by APTE 205 is provided below.

Pharmacy management server 200 may be provided for centralizing various data and/or for providing functionality which would otherwise be provided by the pharmacy computer 100. For example, APTE 205 is included on pharmacy management server 200 so that pharmacy computer 100, and any other pharmacy computer in communication with pharmacy management server 200, has access to APTE 205. APTE may be a module on pharmacy management server 200, wherein the APTE is comprised of software, hardware, firmware, or some combination thereof, being executed on pharmacy management server 200. Pharmacy management server 200 includes a processing unit 206 comprised of a processor 210 and a memory 220. Memory 220 may store software comprised of executable instructions, where processor 210 is configured to execute the executable instructions to implement any one or more process or method described herein (e.g., processes and methods implemented by APTE 205).

Pharmacy management system 1 also may include medical facility computer 400. Medical facility computer 400 may be representative of a computer located at a hospital, doctor's office, urgent care facility, or other medical facility where a medical professional may prescribe medication to a patient. Although not specifically illustrated, medical facility computer 400 may include a network interface configured to enable medical facility computer 400 to communicate (e.g., transmit and receive information) with pharmacy computer 100 and/or pharmacy management server 200 via network 150. For example, medical facility computer 400 may communicate with pharmacy management server 200 in order to transmit prescription information found on the patient's prescription order directly to the APTE 205 on pharmacy management server 200. Medical facility computer 400 is further in communication with an input device 430, such as a keyboard, mouse, barcode scanner, RFID reader, NFC reader, image scanner, memory slot, or other information input device capable of inputting information (e.g., prescription information) into medical facility computer 400. A user at the medical facility may, for example, input prescription information from the prescription order via the keyboard and mouse, or have an optical character recognition (OCR) process executed on an electronic copy of the prescription order to extract the prescription information. It follows that prescription information may be transmitted directly from the medical facility computer 400 to pharmacy management server 200. The prescription information transmitted to pharmacy management server 200 may be in a known electronic format such as eRx. Once received at pharmacy management server 200, the APTE 205 may process the prescription information according to the automated prescription translation process detail herein. A more detailed description of the automated prescription translation process implemented by APTE 205 is provided below.

FIG. 3 illustrates flow chart 300 that describes an automated prescription translation process that may be implemented by APTE 205. The automated prescription translation process is configured to receive electronic prescription information, which may be referred to as eRx throughout this disclosure. The eRx information corresponds to the information found on the prescription order, which may include: medication name information, medication strength or dosage information (e.g., dosage form), medication dispense quantity information (e.g., total number of tablets to dispense), medication usage frequency information, patient identification information (e.g., name, address, age, phone number), prescription date information, medication route of administration, and prescribing doctor identification information (e.g., name, address, phone number, drug enforcement agency information). Throughout this disclosure, SIG information may generally refer to medication administration instruction information.

Figure 18:
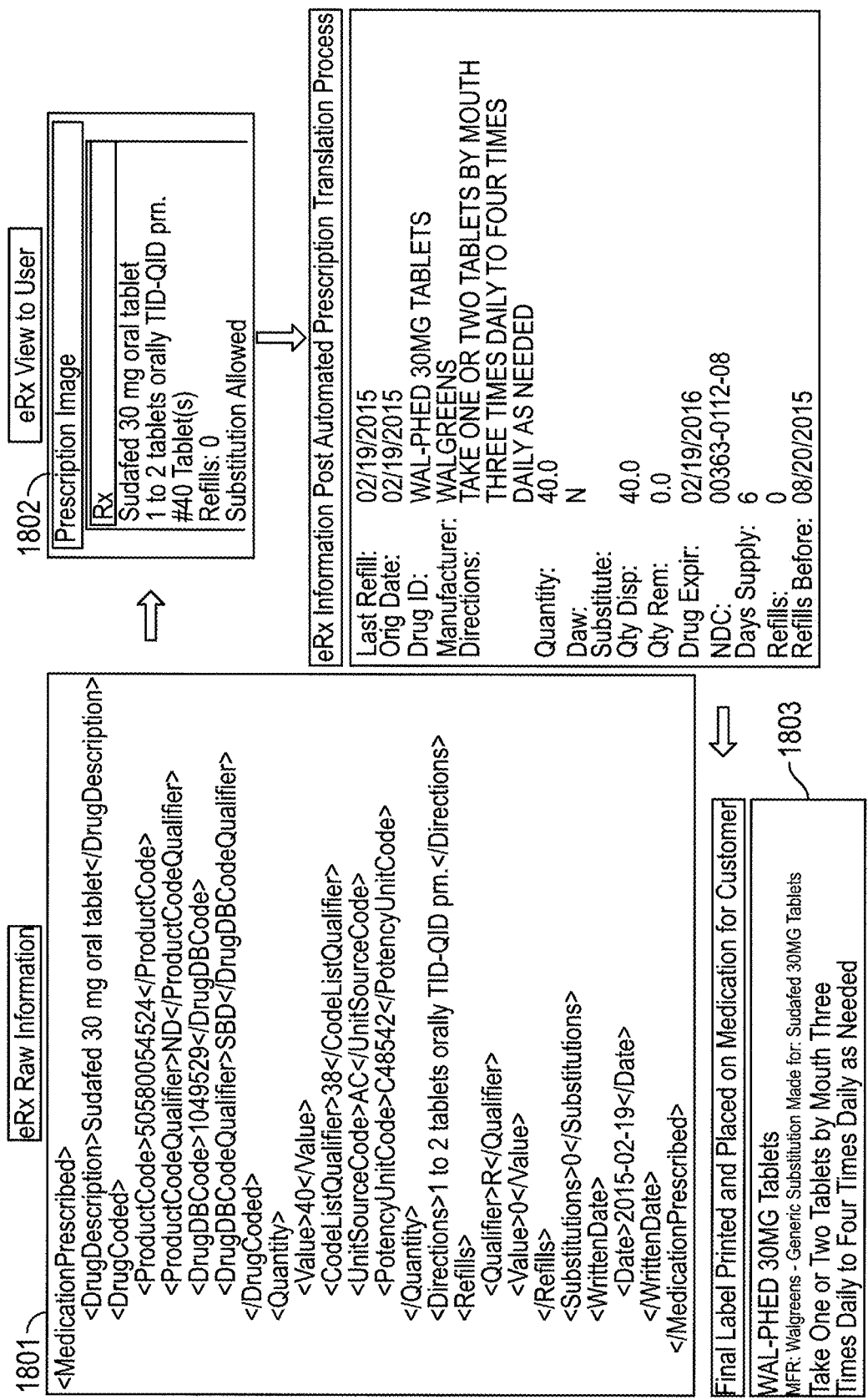
FIG. 18 illustrates a progression of prescription information as the prescription information progresses through the automated prescription translation process, according to some embodiments.

The automated prescription translation process will analyze the eRx information in view of various rules and processes to determine whether the eRx information is acceptable to generate a SIG wrapper (i.e., medication label). If the automated prescription translation process is successful, a final SIG will be output that may be printed on a label for placement on medication packaging. The final SIG will be in a standard format that offers the benefits described earlier. For example, FIG. 18 illustrates an exemplary final SIG wrapper 1803 that may be printed based on eRx information that has been processed according to the automated prescription translation process described herein.

Figure 3A:
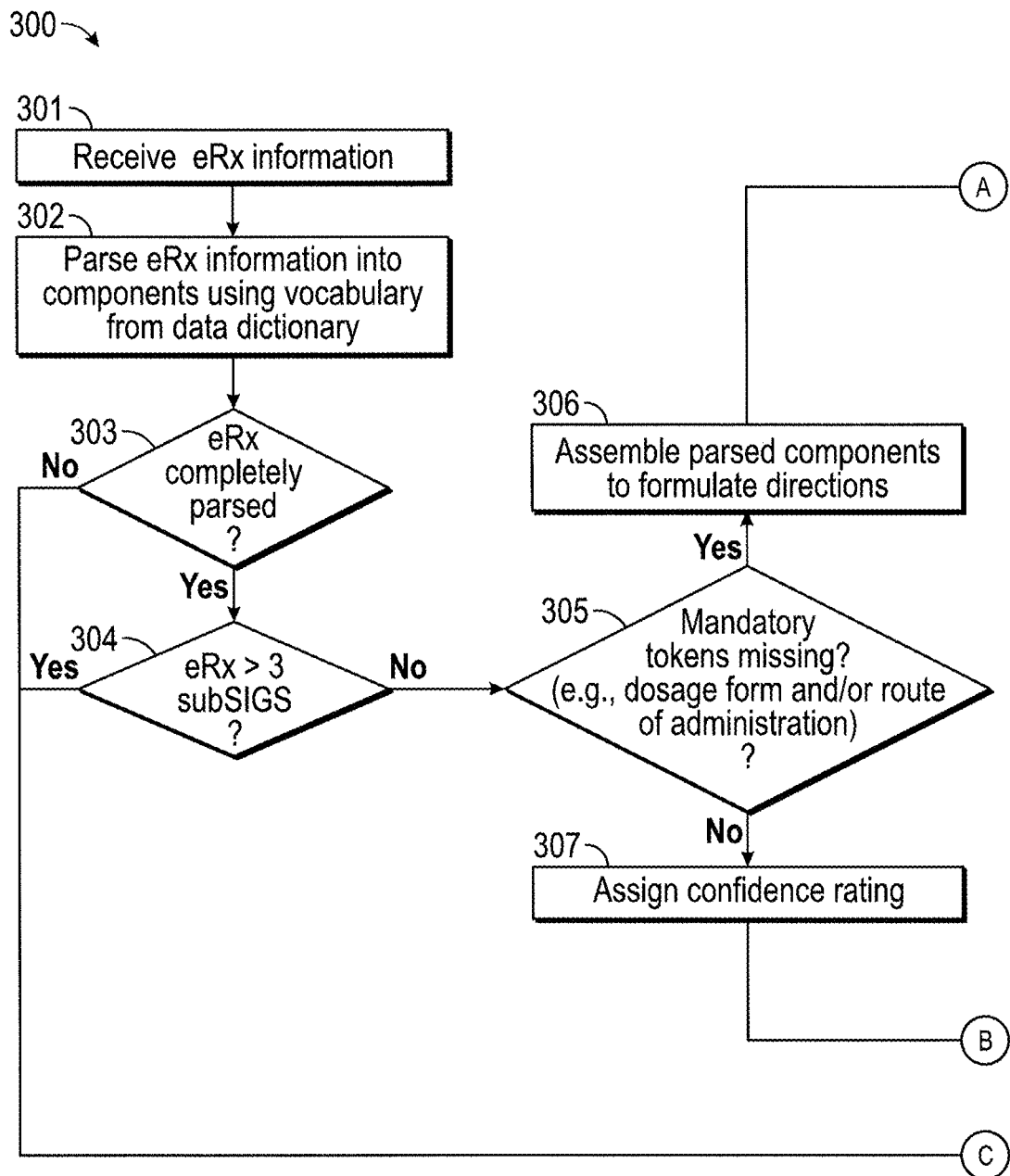
FIG. 3A illustrates a first portion of a flow chart describing an exemplary process for implementing an automated prescription translation process, according to some embodiments.
Figure 3B:
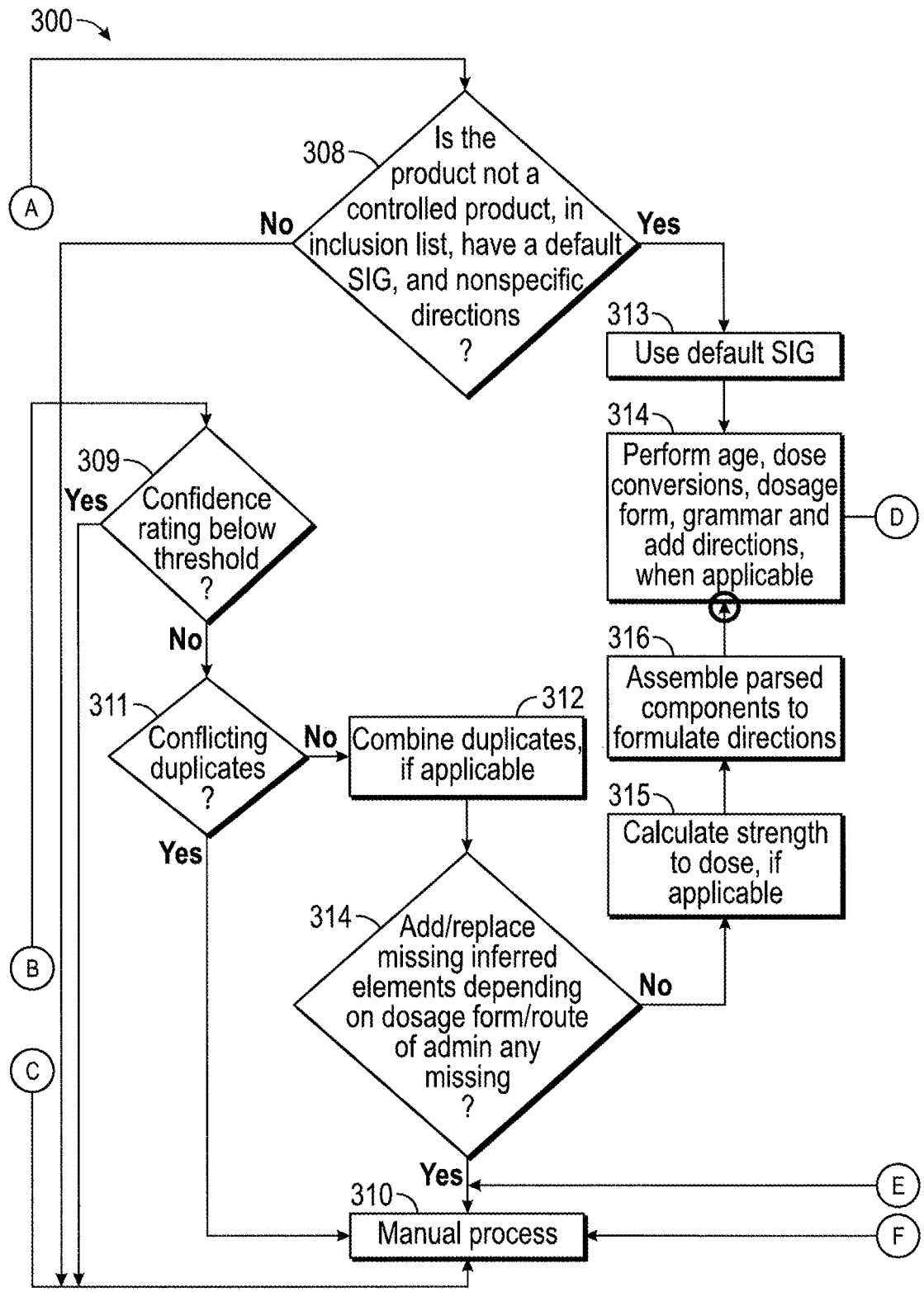
FIG. 3B illustrates a second portion of a flow chart describing the exemplary process for implementing an automated prescription translation process, according to some embodiments.
Figure 3C:
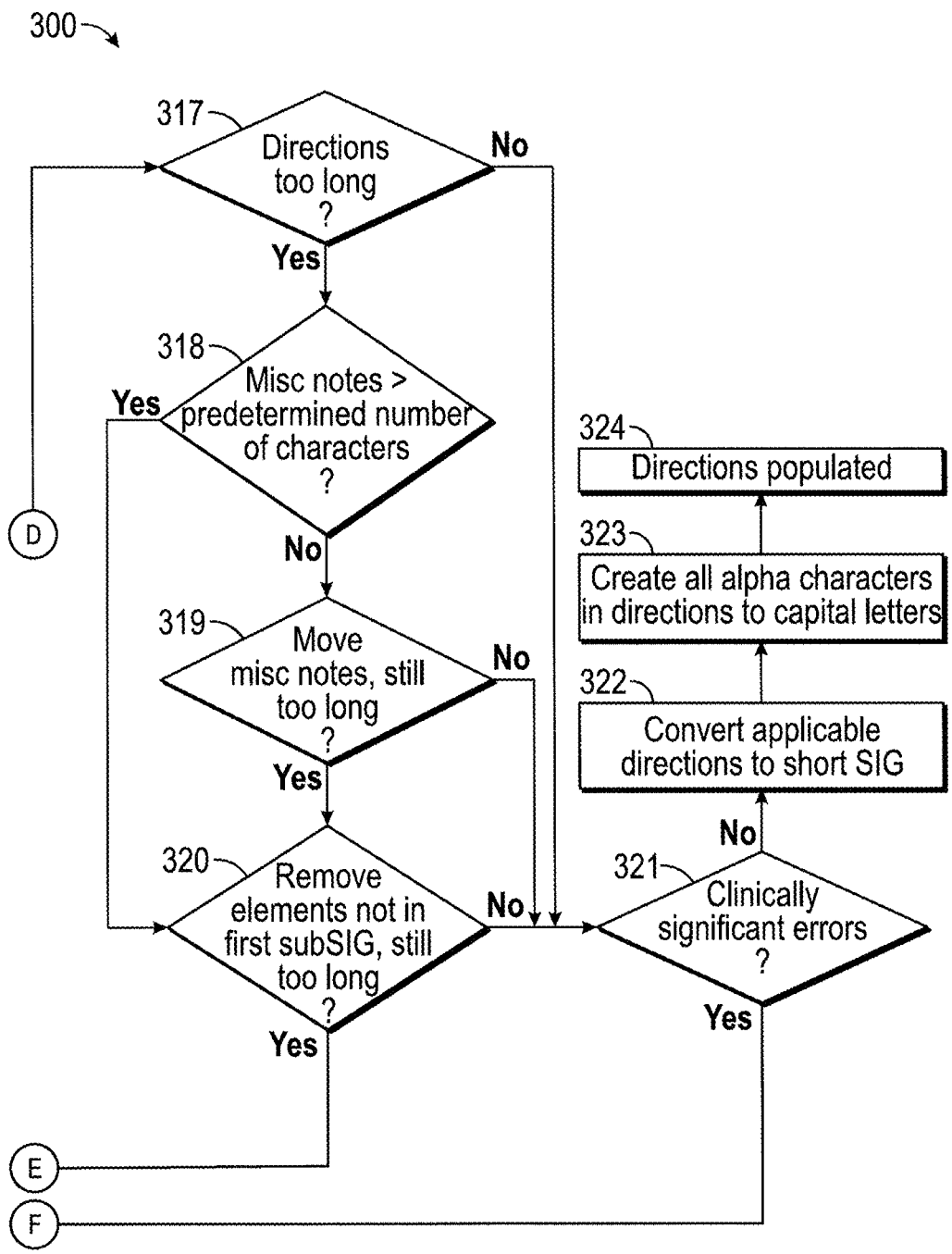
FIG. 3C illustrates a first portion of a flow chart describing the exemplary process for implementing an automated prescription translation process, according to some embodiments.
Figure 4:
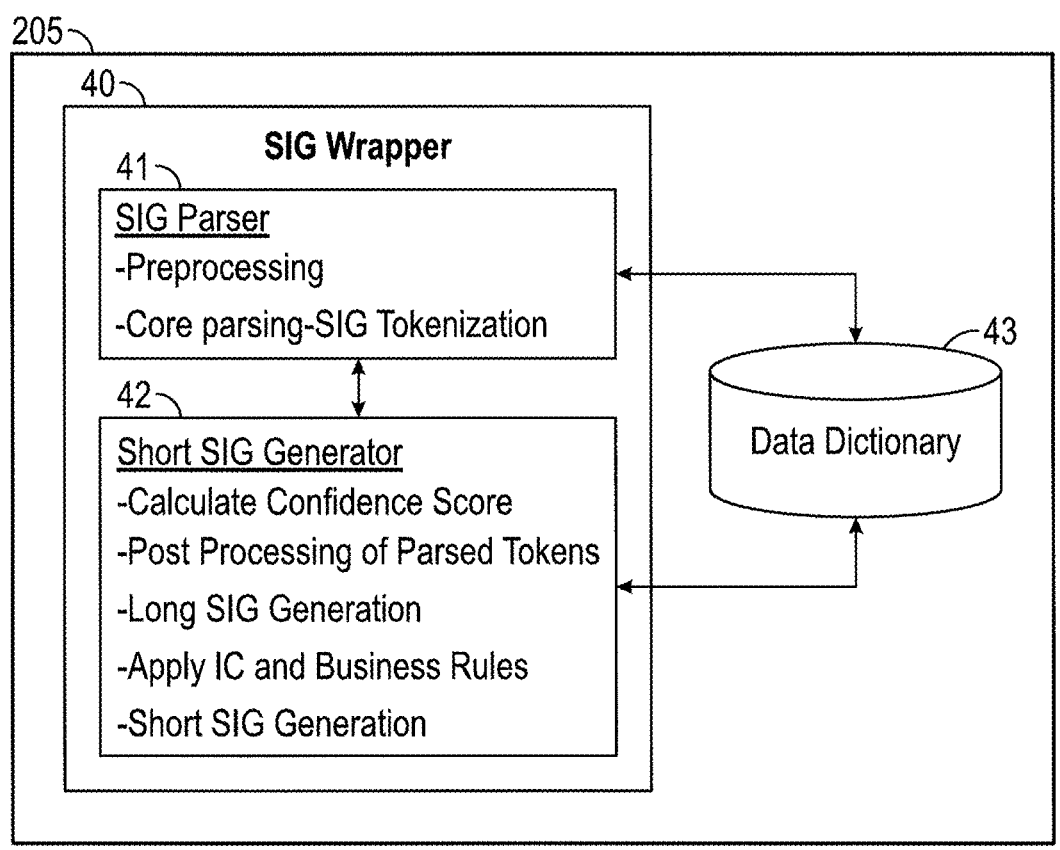
FIG. 4 illustrates a detailed depiction of an automated prescription translation engine for implementing the automated prescription translation process, according to some embodiments.

In order to implement the automated prescription translation process described by flow chart 300 in FIGS. 3A to 3C, APTE 205 may include one or more modules as illustrated in FIG. 4. For example, FIG. 4 depicts APTE 205 as including SIG wrapper module 40 and data dictionary 430. SIG wrapper module 40 further includes SIG parser module 41 and short SIG generator module 42, where both SIG parser module 41 and short SIG generator module 42 are in communication with data dictionary 43 to access information found on data dictionary 430. Data dictionary 43 may be a database or other memory storage unit that stores various definitions (e.g., token definitions, token category definitions) and rules that will be referenced during the automated prescription translation process described herein. SIG wrapper module 40 may utilize SIG parser module 41 to implement a parsing process portion of the automated prescription translation process, and utilize short SIG generator module 42 to implement a SIG generation process portion of the automated prescription translation process, as described with reference to flow chart 300 below.

Referring to flow chart 300, APTE 205 receives eRx information at 301. The eRx information is in an electronic format, and may have been received from a pharmacy (e.g., pharmacy computer 100) or a medical facility (e.g., medical facility computer 400).

At 302, APTE 205 initiates a parsing process on the received eRx information. The parsing at 302 may be implemented by SIG parser module 41. The parsing process looks to categorize tokens identified from the received eRx information into a list of output attributes according to one or more rules. SIG parser module 41 may send the list of output attributes resulting from the parsing process to short SIG generator module 42 as an input to short SIG generator module 42.

SIG parser module 41 may begin the parsing process corresponding to the process at 302 by applying a pre-processing operation to the received eRx information. The pre-processing operation serves to modify the received eRx information into a standard format that will then be provided to a subsequent core parsing operation. The pre-processing operation may include the application of one or more of the pre-processing rules to the received eRx information such as, for example, the pre-processing rules identified in Tables 501-503 (FIGS. 5-7). Each pre-processing rule operates by identifying specific portions within the received eRx information, and modifying the specific portions according to the pre-processing rule. For example some of rules require modifying lowercase letters into uppercase letters, modifying extra spaces between words into single spaces, and replacing certain words, phrases, numbers, or characters with standard words, phrases, numbers, or characters. The specific portions that are identified for modification by the pre-processing rules may correspond to medication administration instructions (i.e., Input SIG information).

The pre-processing rules may be applied by SIG parser module 41 in the order depicted in Tables 501-503, or in another order involving one or more of the pre-processing rules. The received eRx information modified by the pre-processing operation may be considered to be pre-processed eRx information, where the pre-processed eRx information has been modified into a standard format in accordance to applied pre-processing rules during the process implemented at 302.

SIG parser module 41 may take the pre-processed eRx information and input it to the core parsing operation. Generally during the core parsing operation, SIG parser module 41 will reference data dictionary 430 to tag specific words or phrases found in the pre-processed eRx information that correspond to specific attributes pre-stored in data dictionary 430. This way, specific words or phrases identified from the pre-processed eRx information may be tagged as belonging to specific attribute categories found in data dictionary 43. For example, SIG parser module 41 may parse the pre-processed eRx information for special patterns. When SIG parser module 41 identifies a word or phrase (i.e., Input String) from the pre-processed eRx information that matches a special pattern as defined from data dictionary 430, SIG parser module 41 may tag the special word or phrase as having a specific attribute. Each attribute that is tagged on the pre-processed eRx information may then be categorized into an appropriate attribute category. Tables 801-804 (FIGS. 8-11) identify various functions (i.e., core-parsing rules) that may be specifically performed by SIG parser module 41 during the core parsing operation. According to some of the functions described in Tables 801-804, some words or phrases from the pre-processed eRx information may be removed after being tagged with certain attributes (e.g., certain words/phrases tagged with the Miscellaneous Notes attribute, certain words/phrases tagged with the Admin Timings attribute, certain words/phrases tagged with the Frequency Suffix or Frequency Suffix with Every attribute, certain words/phrases tagged with the Strength Units attribute, certain words/phrases tagged with the Dosage Forms attribute, certain words/phrases tagged with the Duration Metrics attribute, certain words/phrases tagged with the Token Category attribute). The functions described in Tables 801-804 may be applied by SIG parser module 41 in the order depicted in Tables 801-804, or in another order involving one or more of the functions. Following the core parsing operation, the pre-processed eRx information may be considered to be core-processed eRx information, where the core-processed eRx information is in a format that includes tagged attributes and/or deleted elements based on the application of the functions applied during the core processing operation. Words or phrases having a tagged attribute may be considered to have a token, or belong to a token category.

SIG parser module 41 may then input the core-processed eRx information into a post-processing operation. Generally, the post-processing operation will perform activities such as parsing the core-processed eRx information and removing words/phrases tagged with an ignorable token or token category. The post-processing operation may also involve identifying non-parsed words/phrases from the core-processed eRx information tagged with an ignorable or removable token or token category. A token may be a specific word or phrase identified from data dictionary 430 that is referenced to compare to words/phrases that comprise the core-processed eRx information. It follows that words or phrases in the core-processed eRx information may be tagged with one or more token attribute. Data dictionary 430 may identify one or more token words or phrases into one or more different token categories (e.g., a verb token category, ignorable token category). Words or phrases in the core-processed eRx information tagged with an ignorable token attribute may be ignored during the post-processing operation, and in some embodiments, may be ignored throughout the subsequent processing of the automated prescription translation process.

SIG parser module 41 may also parse the core-processed eRx information for words or phrases tagged with frequency related attributes, and process such words or phrases to further tag them into a respective frequency attribute token category (e.g., low medication usage frequency value, high medication usage frequency value, medication frequency unit). SIG parser module 41 may also parse the core-processed eRx information for words or phrases tagged with dosage related attributes, and process such words or phrases to further tag them into a respective dosage attribute token category (e.g., low medication dosage value, high medication dosage value, medication dosage unit). SIG parser module 41 may also parse the core-processed eRx information for words or phrases tagged with duration related attributes, and process such words or phrases to further tag them into a respective duration attribute token category (e.g., low usage duration value, high usage duration value, duration unit). SIG parser module 41 may also parse the core-processed eRx information for words or phrases tagged with strength related attributes, and further analyze such words or phrases to further tag them into a respective strength attribute token category (e.g., low medication strength value, high medication strength value, medication strength unit). SIG parser module 41 may also parse the core-processed eRx information for words or phrases tagged with medication administration related attributes, and process such words or phrases to further tag them into a respective medication administration attribute token category (e.g., medication administration frequency, medication administration timing). Tables 1201-1202 (FIGS. 12-13) identify various tagging and categorization rules (i.e., post-processing rules) that may be applied during the post-processing operation. The rules described in Tables 1201-1202 may be applied by SIG parser module 41 in the order depicted in Tables 1201-1202, or in another order involving one or more of the rules.

Following the parsing processes implemented by SIG parser module 41 as described above, one or more of the following elements and/or attributes of the received eRx information may have been parsed and tagged into one or more of the following token categories: verb, low dosage value, high dosage value, dosage unit, low strength value, high strength value, strength unit, route of administration, site of administration, incoming low frequency value, incoming high frequency value, incoming frequency unit, calculated low frequency value, calculated high frequency value, calculated frequency unit, administration timings, auxiliary, low time period value, high time period value, time period unit, additional notes (nonspecific), low duration numeric value, high duration numeric value, duration unit, conjunctions, indications, miscellaneous notes, and unknown words or values. Following the parsing process implemented by SIG parser module 41, the received eRx information has been parsed, modified, and tagged with appropriate tokens, and thus may be considered parsed eRx information.

Following the parsing process implemented by SIG parser module 41, short SIG generator module 42 may be called upon by SIG wrapper module 40 to implement one or more of the remaining processes depicted in flow chart 300. Short SIG generator module 42 may receive the parsed eRx information from SIG parser module 41 to implement one or more of the remaining processes depicted in flow chart 300. As described earlier, the parsed eRx information may be in the format of a list of output attributes that results from the parsing process implemented by SIG parser module 41 on the received eRx information.

At 303, short SIG generator module 42 determines whether the parsed eRx information has been completely parsed. This may involve short SIG generator module 42 determining whether all of the tokens tagged onto the parsed eRx information has been parsed. If there are non-parsed tokens available, then short SIG generator module 42 will flag a manual processing indicator and return the parsed eRx information to SIG wrapper module 400. When SIG wrapper module 40 receives the parsed eRx information with the manual processing indicator, the automated prescription translation process may be stopped and returned to require manual processing as indicated by the automated prescription translation process reverting to step 310. This may be referred to as short SIG generator module 42 reverting to the manual processing.

If short SIG generator module 42 determines all tokens of the parsed eRx information have been parsed, at 303 short SIG generator module 42 determines whether the parsed eRx information contains greater than three subSIGS. A subSIG is defined as a clause or direction found in the eRx information related to medication administration instructions that require one or more steps. If the number of subSIGS is greater than three (duplicate or not), then short SIG generator module 42 will stop the automated prescription translation process and revert to the manual processing at 310. The significance of this subSIG validation step is to determine the complexity of the prescription corresponding to the eRx information. Including more than three clauses or directions may indicate that the prescription is too complex to rely on the automated prescription translation process. Although three subSIGS is identified as the deciding number of subSIGS for reverting back to the manual process at 303, another predetermined number of subSIGS may be referenced.

If the parsed eRx information is determined to have less than three subSIGS, then short SIG generator module 42 proceeds to 305 where a determination is made whether mandatory tokens, or other elements, are missing from the parsed eRx information. For example, a rule may state that medication dosage tokens and/or form of administration tokens are mandatory and need to be included in parsed eRx information. In such cases, short SIG generator module 42 will determine whether medication dosage tokens and/or form of administration tokens are missing from the parsed eRx information. If medication dosage tokens and/or form of administration tokens are missing, short SIG generator module 42 will assign a missing mandatory token indicator to parsed eRx information. According to different embodiments, any one or more of the tags or tokens described herein may be considered to be mandatory.

According to some embodiments, the absence of information related to a mandatory tag or token in the parsed eRx information will cause the automated prescription translation process to revert to the manual process at 310. According to other embodiments, if one or more mandatory tokens are determined to be missing, short SIG generator module 42 proceeds to 306 where parsed components of the parsed eRx information are assembled to formulate directions (i.e., directions for using/administering medication identified in the prescription). The directions may be referred to as long SIG, and may be formulated immediately upon determining one or more mandatory tokens are missing. The directions may be formed in a grammar based order as defined by a corresponding requirements rule. Long SIG will be formed by concatenating attributes of the parsed eRx information in the order defined by the requirements rule with space between the attributes. Arranging the attributes in the order defined by the business requirement rule may be required to properly implement the automated prescription translation process.

After formulating the long SIG, short SIG generator module 42 may validate the following conditions at 308 (FIG. 3B): determine whether medication identified in parsed eRx information is, or is not, a controlled drug according to applicable drug class laws; determine whether medication identified in parsed eRx information has a default SIG; determine whether medication identified in parsed eRx information is located in a configurable inclusion list (a configurable default SIG inclusion list may be based on national drug code (NDC) or generic product identifier (GPI). The configurable inclusion list may be referenced to check whether the selected NDC/GPI is available in configurable Inclusion List. Here, a determination is made as to whether whole formulated long SIG matches nonspecific directions (formulated long SIG should match completely with one of the directions on a Nonspecific Directions list). If a predetermined number of the conditions (e.g., all of the conditions) are validated, the default SIG may be used when one or more mandatory tokens have been found missing. For example, if the original directions found in the parsed eRx information is determined to be overly general (e.g., "use as directed"), a default SIG, when available for the specific medication, may replace the original directions. The default SIG may be a set of default medication administration instructions that are stored on data dictionary 430 to be applied for specific medications. Typically, medications having a default SIG stored in the data dictionary 430 can be considered to be "common medications" where the administration instructions are commonly known. If the default SIG is used, short SIG generator module 42 will flag a default SIG indicator that indicates the default SIG is being used for the medication identified in the parsed eRx information. Also if the formulated long SIG has nonspecific directions, then short SIG generator module 42 may flag a Nonspecific SIG Indicator and return to SIG wrapper module 400. The Nonspecific SIG Indicator may be used later in a days supply process (e.g., a default number of days of supply for the medication may be used if the original directions are not specific). If all of the conditions are not validated, and a default SIG is not available, short SIG generator module 42 may flag the manual processing indicator and revert the automated prescription translation process to the manual process at 310.

If the default SIG is used at 313, then short SIG generator module 42 will send the default SIG to SIG parser module 41. SIG parser module 41 may then implement the parsing process described herein with reference to step 302 on the default SIG. After implementing the parsing process on the default SIG, a list of output attributes may be sent to short SIG generator module 42, where short SIG generator module 42 will perform the processes described at step 314. At 314, an age determination may be implemented to determine the age of the patient taking the medication identified in the parsed eRx information. If the patient is determined to be a child (e.g., age of patient is less than 13 years old), then an adult is assumed to be administering the medication to the child patient. Therefore, a verb conversation is applied to verbs that would change, for example, "take" to "give" so that the directions can be properly read by the adult administering the medication to the child patient. At 314, a dosage form conversion may also be applied that takes a dosage identified in the parsed eRx information in one unit (e.g., ml) and converts it to another unit (e.g., number of tablets). The dosage form conversion may be applied especially in situations where the original dosage unit identified in the parsed eRx information is easily converted to the second dosage unit (e.g., original dosage is 10 ml and a tablet is known to be 10 ml, so the dosage may be converted from 10 ml to 1 tablet). The dosage conversion may also check to ensure that a dosage form (e.g., tablet) initially identified to correspond to the medication remains consistent throughout the directions. For example, if the original directions identify a capsule dosage form, the dosage form conversion may convert any subsequent use of another dosage form (e.g., tablet instead of capsule) in the administration directions back to the capsule dosage form initially identified in the mediation administration instructions. A grammar conversion may also be applied to fix any grammatical mistakes found in the parsed eRx information at 314.

Reverting back to step 305, if all mandatory tokens are determined not to be missing at 305, short SIG generator module 42 proceeds to 307 where a confidence score is calculated and assigned to the parsed eRx information. A confidence score calculator may be called by the short SIG generator module 42 to calculate the confidence score. The confidence score calculator may begin with a default confidence score (e.g., 100), and then decrease each time a decreasing factor is found in the parsed eRx information. For example, the confidence score calculator may decrease the confidence score by a predetermined amount if a mandatory element or token is not found in the parsed eRx information. The decreasing value may be higher for each additional mandatory element or token that is found missing. The confidence score calculator may also decrease the confidence score by a predetermined amount for each subSIG identified in the parsed eRx information. The confidence score calculator may also decrease the confidence score by a predetermined amount when a dosage value range is identified rather than a fixed dosage value amount within the parsed eRx information. The confidence score calculator may also decrease the confidence score by a predetermined amount when a fraction is identified within the parsed eRx information. The confidence score calculator may also decrease the confidence score by a predetermined amount when the parsed eRx information includes more than a predetermined number of words. The confidence score calculator may also decrease the confidence score by a predetermined amount when a miscellaneous note is identified within the parsed eRx information. The confidence score calculator may also decrease the confidence score when a secondary inferred value is identified within the parsed eRx information. Some decreasing factors may decrease the confidence score more than others.

After calculating the confidence score at 307, the confidence score is compared to a threshold value at 309 to determine whether the confidence score is below the threshold value. If the confidence score is below the threshold value, short SIG generator module 42 sends the parsed eRx information to the SIG wrapper module 40 to revert the automated prescription translation process to the manual process at step 310. At some point, short SIG generator module 42 may convert fractions found within parsed eRx information into decimals.

After determining the confidence score is above the threshold value at 309, short SIG generator module 42 proceeds to 311 where one or more duplicate SIG and/or duplicate subSIG rules may be applied to the parsed eRx information. A list of exemplary duplicate SIG and duplicate subSIG rules (i.e., the duplicate rules) are depicted in Tables 1401 and 1402 (FIGS. 14-15). During the application of the duplicate rules, certain duplicate rules may cause short SIG generator module 42 to send the parsed eRx information to SIG wrapper module 40 to revert to the manual process at 310. If a duplicate rule does not cause short SIG generator module 42 to revert to the manual process, then the automated prescription translation process may proceed to 312 where duplicates may be combined as applicable.

After 312, short SIG generator module 42 may add or replace missing inferred tokens in the parsed eRx information related to dosage form and/or route of administration information corresponding to a medication identified in the parsed eRx information as follows: add inferred primary element(s) based on confidence rating rules and by referring to a mandatory or inferred token list in case the element is missing from parsed eRx information; replace the parsed element with a primary inferred element in case the element is present as the secondary inferred element in the mandatory or inferred token list; and if the input parsed element is not a primary or secondary element, then the manual processing indicator will be set and returned to the SIG wrapper module 40 to mark the parsed eRx information for manual processing at 310. So for a given medication identified in the parsed eRx information (e.g., a 24 hour orally administered capsule), the medication may be tagged with one or more token attributes. For example, the medication may be tagged with a mandatory token requiring the parsed eRx information to include information for a high strength value and a low strength value. If the parsed eRx information does not include the mandatory token, the automated prescription translation process may revert to the manual process at 310. The given medication may also have one or more primary or secondary inferred tokens attached to the parsed eRx information. If an inferred token is attached to the parsed eRx information, the inferred token information may be inserted into the parsed eRx information if it is not already present in the parsed eRx information. For example, the 24 hour orally administered capsule may be missing a route of administration information, however data dictionary 430 may have stored a primary inferred token for the route of administration token attribute such that if the rout of administration information is missing from the parsed eRx information, the primary inferred route of administration token attribute (e.g., "by mouth") may be inserted into the parsed eRx information. If the route of administration corresponding to the primary inferred token attribute (e.g., "by mouth") is not included in the parsed eRx information, other routes of administration that found in the parsed eRx information may be accepted if they correspond to at least a secondary inferred token attribute (e.g., "orally, oral, mouth").

If the adding and replacing inferred tokens step is successful, then at 325 short SIG generator module 42 may implement a strength to dose conversion. In other words, a strength token associated to the parsed eRx information will be converted to a dose. The strength to dose conversion will be based on the following parameters: Single Active Ingredient indicator, Configurable strength conversion exclusion list maintained, and Configurable strength conversion inclusion list. The strength may be converted to a dose, and vice versa, based on a drug strength parameter and a drug strength unit of measure (UOM) parameter. For example, if the UOM identified in the parsed eRx information is "25 ml", this UOM may be converted to "1 tablet" if the tablet corresponds to a 25 ml dosage. By including this step, the resulting final SIG wrapper (i.e., prescription instruction wrapper) produced for the consumer may be easier to read.

Following the strength to dose conversion at 315, short SIG generator module 42 may assemble parsed components of the parsed eRx information to formulate directions (i.e., long SIG) at 316. Long SIG will be formed by concatenating parsed attributes of the parsed eRx information in an order defined in a token attribute order with space between attributes. The SIG order may be defined as: 1) If the parsed token contains dose and not strength, display dose in directions; 2) If the parsed token provides strength and not dose, display dose in directions after conversion to default SIG at 308; 3) If the parsed token provides both strength and dose, display both strength and dose in directions with the strength in parenthesis; 4) If product is in inclusion list, display only strength in directions and not in parenthesis; and 5) Generate the long Sig based on the rules defined for subSigs; 6) Return the long Sig for every subSigs; 7) Return the dose to a process management service when a final SIG displays the strength; 8) Need to display only the incoming time period in the final output if the calculated frequency and the inverse of the calculated time period are equal and the incoming frequency and the incoming time period are present in the received eRx information else need to display both the incoming time period and the incoming frequency in the final SIG. The process management service may be a third party vendor, or part of the APTE 205, configured to ensure each of the requirements rules are implemented on the eRx information, and ensure the final SIG wrapper output is transmitted and received by the pharmacy computer 100.

After a formulated direction has been formulated at 316, short SIG generator module 42 may proceed to a plurality of direction validation steps. For example, short SIG generator module 42 may determine whether the formulated direction is too long by checking if the formulated direction has a length greater than one hundred and fifty (150) characters at 317. If the formulated direction is not too long at 317, short SIG generator module 42 will proceed to 321. If the formulated direction is too long at 317, short SIG generator module 42 may check whether miscellaneous notes exist or not and determine whether such miscellaneous notes are greater than fifty (50) characters at 318. If miscellaneous notes are greater than fifty (50) characters at 318, short SIG generator module 42 may remove elements from parsed eRx information not in a first subSig, and then determine whether the formulated direction is still too long (e.g., greater than one hundred and fifty (150) characters) at 320. If the formulated direction is still too long at 320, short SIG generator module 42 will revert to the manual process at 310. If the formulated direction is not too long at 320, short SIG generator module 42 will proceed to 321. If the miscellaneous notes are not greater than 50 at step 318, then short SIG generator module 42 will proceed to 319. At 319, short SIG generator module 42 will move the part in the miscellaneous notes (a component in the SIG) out of the SIG and save it in a separate field (one time label comments), which will be passed as a separate output field in the automated prescription translation process where IC+ rules may be applied. After the process at 319, if the formulated direction is still too long, short SIG generator module 42 will proceed to 320.

Figure 16B:

At 321, short SIG generator module 42 will check for clinically significant errors in a validation step. Clinically significant errors may apply to one or more of the following: 1) If the selected medication's route of administration (from process management service) does not match with route of Administration in the formulated directions, and the medication is not in the configurable route of an administration mismatch inclusion list, then the manual processing indicator will be set and returned to the SIG wrapper module 40 to mark the SIG for manual processing at 310; 2) The system will continue with the automated prescription translation process, if the medication's route of administration does not match the formulated directions, but the medication is on a configurable inclusion list (route of admin mismatch product inclusion list); and 3) The manual process at 310 will be invoked if strength and dose are both on the formulated directions and they are not equal conversions. In this case the manual processing indicator will be set and returned to the SIG wrapper module 40 to mark the SIG for manual processing at 310. This step will not be performed if the clinically significant errors are checked after the parsing of default SIG. For example, a mismatch is where a drug dosage form (e.g., oral tablet) is directed to be administered in a form that doesn't match with the drug dosage form (e.g., topically); however certain medications/drugs may belong to the Inclusion List so that certain mismatches identified in the Inclusion List can be ignored and allowed to proceed. FIGS. 16A and 16B illustrates table 1601 that identifies additional exemplary errors and their corresponding error codes that may be identified by short SIG generator module 42 at step 321, where the identification of one or more of the errors identified in table 1601 may cause the automated prescription translation process to cease and revert to the manual process at 310. FIGS. 17A and 17B illustrates table 1602 that identifies additional exemplary errors and their corresponding error codes that may be identified by short SIG generator module 42 at step 321, where the identification of one or more of the errors identified in table 1602 may cause the automated prescription translation process to cease and revert to the manual process at 310.

If the clinically significant validation is successful at 321, one or more IC+ rules may be implemented as follows: modify the formulated directions based on dosage form and patient age; apply proper usage of singular and plural words; translate parsed (transmitted) dosage form based on the selected medication dosage form if the parsed dosage form is different than selected medication dosage form (this may only apply to Tablet and Capsule forms).

At 322, short SIG generator module 42 will convert the parsed eRx information and/or the formulated directions to a short SIG format. This process includes converting the long SIG format into the short SIG format by matching portions of the long SIG format to corresponding words or phrases found in data dictionary 430, and replacing matched words or phrases accordingly to achieve the short SIG format.

At 323, short SIG generator module 42 will convert all alpha characters within the formulated directions to capital letters.

At 324, a final SIG will be outputted that includes directions for patients as found in the original order prescription. The final SIG may then be transmitted to pharmacy computer 100 or medical facility computer 400 to be placed on a medication package.

In terms of hardware architecture shown in FIG. 2, the computers and servers mentioned in FIG. 2 may include any combination of a processor, memory, database, software module, as well as one or more input and/or output (I/O) devices communicatively coupled via a communication interface. The communication interface can be, for example, but not limited to, one or more buses or other wired or wireless connections, as is known in the art. The communication interface may have additional elements, which are omitted for simplicity, such as controllers, buffers (caches), drivers, repeaters, and receivers, to enable communications. Further, the interface may include address, control, and/or data connections to enable appropriate communications among the other computer components.

The processors described as being included within the various processing units 106, 206, and 406, may be hardware devices for executing software, particularly software stored in a memory, such as the memory described as being included within the various processing units 106, 206, and 406. The processor can be any custom-made or commercially available processor, a central processing unit (CPU), an auxiliary processor among several processors associated with computers 200, 400, or server 300, a semiconductor-based microprocessor (in the form of a microchip or chip set), a microprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, SQL, Smalltalk, APL, KLisp, Snobol, Developer 200, MUMPS/Magic.

The memory or storage devices described herein may include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory may incorporate electronic, magnetic, optical, and/or other types of storage media. The memory can have a distributed architecture where various components are situated remote from one another, but are still accessed by the processors. It should be noted that the databases described herein may be a collection of information/data arranged in a known or predictable manner, wherein the information/data is stored on a memory.

The various modules described herein may include one or more separate software programs or modules. The software programs stored in memory such as memory 120, 220, and 420, may comprise ordered listings of executable instructions for implementing logical functions that may be executed by the processor included in the corresponding processing units 106, 206, and 406, or other processor described herein. Memory 120, 220, and 420, may also include a suitable operating system (O/S). A non-exhaustive list of examples of suitable commercially available operating systems is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run-time Vxworks operating system from WindRiver Systems, Inc.; or (g) an appliance-based operating system, such as that implemented in hand-held computers or personal digital assistants (PDAs) (e.g., PalmOS available from Palm Computing, Inc., and Windows CE available from Microsoft Corporation). The operating system essentially controls the execution of other software programs by a processor, and provides scheduling, input-output control, file and data management, memory management, and communication control and related services.

The software programs that comprise the modules described herein may be a source program, executable program (object code), script, or any other entity comprising a set of instructions to be performed. When using a source program, the program needs to be translated via a compiler, assembler, interpreter, or the like, which may or may not be included within the memory, so as to operate properly in connection with the O/S. Furthermore, the software programs described herein may be written as (a) an object-oriented programming language, which has classes of data and methods, or (b) a procedural programming language, which has routines, subroutines, and/or functions, for example but not limited to C, C++, Pascal, Basic, Fortran, Cobol, Perl, Java, and Ada. In one embodiment, the software programs may be written in Cow, Java and/or html for use with client type I/O devices.

Each of the computing devices, input devices, and/or other devices described herein as including a processing unit may further include one or more I/O components (i.e., an input output component). The I/O component may, for example, be a keyboard, mouse, scanner, microphone, touch screens, interfaces for various communications devices, barcode readers, stylus, laser readers, radio-frequency device readers, etc. Furthermore, the I/O components may also include output devices, for example but not limited to a printer, barcode printers, displays, etc. Finally, the I/O components may further include devices that communicate both inputs and outputs, for instance but not limited to a modulator/demodulator (modem; for accessing another device, system, or network), a radio frequency (RF) or other transceiver, a telephonic interface, a bridge, a router, and other devices that allow for wired, or wireless, communication of data and/or information.

If pharmacy computer 100, medical facility computer 400, or pharmacy management server 200 is a PC, workstation, PDA, or the like, the software in the memory may further include a basic input output system (BIOS). The BIOS is a set of essential software routines that initialize and test hardware at startup, start the O/S, and support the transfer of data among the hardware devices. The BIOS is stored in ROM so that the BIOS can be executed when the computer is activated.

When pharmacy computer 100, medical facility computer 400, or pharmacy management server 200 is in operation, the respective processors are configured to execute software stored within the memory of corresponding processing units 106, 206, and 406, to communicate data to and from corresponding memory, and to generally control operations of the respective pharmacy computer 100, medical facility computer 400, or pharmacy management server 200, pursuant to the software.

It should be noted that the software programs described herein can be stored on any computer-readable medium for use by or in connection with any computer-related system or method. In the context of this disclosure, a "computer-readable medium" may be an electronic, magnetic, optical, electromagnetic, infrared, or semiconductor system, apparatus, device, or propagation medium, or other physical device or means that can contain or store a computer program for use by or in connection with a computer related system or method. In the context of this disclosure, a "computer-readable medium" may also be any product that can store, communicate, propagate, or transport the program for use by or in connection with the instruction execution system, apparatus, or device. More specific examples of a computer-readable medium (a non-exhaustive list) include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Any process descriptions or blocks in the figures, should be understood as representing modules, segments, or portions of code which include one or more executable instructions for implementing specific logical functions or steps in the process, and alternate implementations are included within the scope of the embodiments described herein, in which functions may be executed out of order from that shown or discussed, including substantially concurrently or in reverse order, depending on the functionality involved, as would be understood by those having ordinary skill in the art.

It should be emphasized that the above-described embodiments, particularly, any "preferred" embodiments, are possible examples of implementations, merely set forth for a clear understanding of the principles of the invention. Many variations and modifications may be made to the above-described embodiment(s) without substantially departing from the spirit and principles of the techniques described herein. All such modifications are intended to be included herein within the scope of this disclosure and protected by the following claims.

What is claimed is:

1. A computing system to automatically produce a medication label that includes prescription information and instructions in a standardized format, the computing system comprising:
   a translation rules and token category definitions data receiving module stored on a memory of a pharmacy management server that, when executed by a processor of the pharmacy management server, cause the processor of the pharmacy management server to receive a plurality of translation rules and token category definitions;
   a prescription information receiving module stored on the memory of the pharmacy management server that, when executed by the processor of the pharmacy management server, causes the processor of the pharmacy management server to automatically receive prescription information from a remote medical facility computing device in response to a medical professional entering the prescription information via a user interface of the remote medical facility computing device, wherein the prescription information defines a medical facility prescription format;
   an automatic prescription translation module stored on the memory of the pharmacy management server that, when executed by the processor of the pharmacy management server, causes processor of the pharmacy management server, in response to receiving the prescription information, to:
   parse the prescription information;
      in response to the parsing, determine whether an exit condition is satisfied for ceasing the automated prescription translation process; and
      control the automated prescription translation process to cease when the exit condition is satisfied, wherein the exit condition is satisfied if more than three directions for administering a medication is identified in the prescription information;
      in response to the parsing, and when the exit condition is not satisfied, tag a word included in the prescription information that satisfies a token category definition with a corresponding token;
      modify the prescription information by modifying the word tagged with the token according to a translation rule corresponding to the token; and
      generate a final instruction wrapper including the modified prescription information; and
   a final instruction wrapper transmission module stored on the memory of the pharmacy management server that, when executed by the processor of the pharmacy management server, causes the processor of the pharmacy management server to transmit the final instruction wrapper to a pharmacy computer system; and
   a medication label module that, when executed, causes a printer, that is locally connected to the pharmacy computer system to automatically produce the medication label, including the prescription information and instructions in a standardized format, based on the final instruction wrapper, in response to the processor of the pharmacy management server transmitting the final instruction wrapper.

2. The computing system of claim 1, wherein the word includes at least one lowercase letter and the token is a lowercase letter token; and wherein the processor is configured to modify the word according to a pre-processing translation rule that modifies the at least one lowercase letter included in the word into an uppercase letter.

3. The computing system of claim 1, wherein the word includes at least one extra space in-between a next word in the prescription information and the token is an extra space token; and wherein the processor is configured to modify the word according to a pre-processing translation rule that modifies the at least one extra space into a single space.

4. The computing system of claim 1, wherein the word includes at least one specified word, phrase, number, or character prestored in the data storage unit and the token is a specified replacement token; and wherein the processor is configured to modify the word according to a pre-processing translation rule that modifies the at least one specified word, phrase, number, or character with a corresponding standard word, phrase, number, or character prestored in the data storage unit.

5. The computing system of claim 1, wherein the processor is configured to: tag a word in the prescription information identified as belonging to a removable word token category with a removable word token; parse the prescription information and identify words in the prescription information tagged with the removable word token; and modify the prescription information by removing words in the prescription information identified as being tagged with the removable word token.

6. The computing system of claim 1, wherein the processor is configured to: control a first computing module to: parse the prescription information; in response to the parsing, tag the word included in the prescription information that satisfies the token category definition with the corresponding token; control a second computing module to: modify the prescription information by modifying the word tagged with the token according to the translation rule corresponding to the token; and generate the final instruction wrapper including the modified prescription information.

7. The computing system of claim 1, wherein the final instruction wrapper is in a standard format for printing on a label and includes administration instructions for administering a medication identified in the prescription information.

8. A computer-implemented method for automatically translating prescription information and automatically producing a medication label that includes prescription information and instructions in a standardized format, the method comprising:
   a translation rules and token category definitions storage module that, when executed by a processor of a pharmacy management server to store a plurality of translation rules and token category definitions in a data storage unit of the pharmacy management server;
   a prescription information receiving module that, when executed by the processor the pharmacy management server, causes the processor of the pharmacy management server to receive prescription information from a remote medical facility computing device in response to a medical professional entering the prescription information via a user interface of the medical facility computing device, wherein the prescription information defines a medical facility prescription format;
   a prescription translation module that, when executed by the processor of the pharmacy management server, causes the processor of the pharmacy management server to:
   parse the prescription information;
   in response to the parsing, determine whether an exit condition is satisfied for ceasing the automated prescription translation process; and
   control the automated prescription translation process to cease when the exit condition is satisfied, wherein the exit condition is satisfied if more than three directions for administering a medication is identified in the prescription information;
   in response to the parsing, and when the exit condition is not satisfied, tag a word included in the prescription information that satisfies a token category definition with a corresponding token;
   modify the prescription information by modifying the word tagged with the token according to a translation rule corresponding to the token;
   generate a final instruction wrapper including the modified prescription information; and
   automatically produce, using a printer locally connected to a pharmacy computer, the medication label including the prescription information and instructions in a standardized format, based on the final instruction wrapper, in response to receiving the final instruction wrapper from the pharmacy management server.

9. The method of claim 8, wherein the word includes at least one lowercase letter and the token is a lowercase letter token; and wherein controlling the processor to modify the word includes modifying the word according to a pre-processing translation rule that modifies the at least one lowercase letter included in the word into an uppercase letter.

10. The method of claim 8, wherein the word includes at least one extra space in-between a next word in the prescription information and the token is an extra space token; and wherein controlling the processor to modify the word includes modifying the word according to a pre-processing translation rule that modifies the at least one extra space into a single space.

11. The method of claim 8, wherein the word includes at least one specified word, phrase, number, or character prestored in the data storage unit and the token is a specified replacement token; and wherein controlling the processor to modify the word includes modifying the word according to a pre-processing translation rule that modifies the at least one specified word, phrase, number, or character with a corresponding standard word, phrase, number, or character prestored in the data storage unit.

12. The method of claim 8, further comprising controlling the processor to control the automated prescription translation process to: tag a word in the prescription information identified as belonging to a removable word token category with a removable word token; parse the prescription information and identify words in the prescription information tagged with the removable word token; and modify the prescription information by removing words in the prescription information identified as being tagged with the removable word token.

13. The method of claim 8, further comprising controlling the processor to control the automated prescription translation process to assign a default score to the prescription information.

14. The method of claim 8, wherein the exit condition is satisfied when a mandatory element corresponding to a medication identified in the prescription information is not also included in the prescription information.

15. The method of claim 8, wherein controlling the processor to control the automated prescription translation engine module includes: controlling a first computing module to: parse the prescription information; in response to the parsing, tag the word included in the prescription information that satisfies the token category definition with the corresponding token; and controlling a second computing module to: modify the prescription information by modifying the word tagged with the token according to the translation rule corresponding to the token; and generate the final instruction wrapper including the modified prescription information.

16. The method of claim 8, wherein the prescription information is based on information obtained from an optical character recognition process implemented on a prescription note at the remote computing device.

17. The method of claim 8, wherein the final instruction wrapper is in a standard format for printing on a label and includes administration instructions for administering a medication identified in the prescription information.

18. A non-transitory computer-readable medium storing computer-readable instructions that, when executed by a processor, cause the processor to automatically produce a medication label that includes prescription information and instructions in a standardized format, the non-transitory computer-readable medium comprising:
- a translation rules data storage module that, when executed by a processor of a pharmacy management server, causes the processor of the pharmacy management server to store a plurality of translation rules and token category definitions on a memory of the pharmacy management server;
- a prescription information data receiving module that, when executed by the processor of the pharmacy management server, causes the processor of the pharmacy management server to receive prescription information data in response to a medical professional entering the prescription information via a user interface of a medical facility computing device, wherein the prescription information defines a medical facility prescription format;
- an automated prescription translation module that, when executed by the processor of the pharmacy management server, causes the processor of the pharmacy management server to:
- parse the prescription information;
  - in response to the parsing, determine whether an exit condition is satisfied for ceasing the automated prescription translation process; and
  - control the automated prescription translation process to cease when the exit condition is satisfied, wherein the exit condition is satisfied if more than three directions for administering a medication is identified in the prescription information;
  - in response to the parsing, and when the exit condition is not satisfied, tag a word included in the prescription information that satisfies a token category definition with a corresponding token;
  - modify the prescription information by modifying the word tagged with the token according to a translation rule corresponding to the token;
  - generate a final instruction wrapper including the modified prescription information; and
  - transmit the final instruction wrapper to a pharmacy computing device; and
- a medication label production module that, when executed by a processor of the pharmacy computing device, causes the processor of the pharmacy computing device to, in response to receiving the final instruction wrapper from the pharmacy management server, automatically produce the medication label via a printer that is locally connected to the pharmacy computing device, wherein the medication label includes the prescription information and instructions in a standardized format, based on the final instruction wrapper.

19. The non-transitory computer-readable medium of claim 18, wherein the word includes at least one lowercase letter and the token is a lowercase letter token, and wherein the processor is further configured to modify the word according to a pre-processing translation rule that modifies the at least one lowercase letter included in the word into an uppercase letter.

20. The non-transitory computer-readable medium of claim 18, wherein further execution of the instructions causes the processor to:
- tag a word in the prescription information identified as belonging to a removable word token category with a removable word token;
- parse the prescription information and identify words in the prescription information tagged with the removable word token; and
- modify the prescription information by removing words in the prescription information identified as being tagged with the removable word token.

* * * * *